United States Patent
Watts et al.

(10) Patent No.: US 11,291,383 B2
(45) Date of Patent: Apr. 5, 2022

(54) MAGNETIC RESONANCE IMAGING PATIENT TEMPERATURE MONITORING SYSTEM AND RELATED METHODS

(71) Applicant: RTTHERMAL, LLC, West Palm Beach, FL (US)

(72) Inventors: Raymond C. Watts, West Palm Beach, FL (US); Stephen F. Blackler, III, Plainfield, IL (US); Jack A. Dekkinga, Jenison, MI (US); James J. Kumler, Jupiter, FL (US)

(73) Assignee: RTTHERMAL, LLC, West Palm Beach, FL (US)

( * ) Notice: Subject to any disclaimer, the term of this patent is extended or adjusted under 35 U.S.C. 154(b) by 470 days.

(21) Appl. No.: 15/522,976

(22) PCT Filed: Oct. 30, 2015

(86) PCT No.: PCT/US2015/058184
§ 371 (c)(1),
(2) Date: Apr. 28, 2017

(87) PCT Pub. No.: WO2016/069967
PCT Pub. Date: May 6, 2016

(65) Prior Publication Data
US 2018/0271396 A1    Sep. 27, 2018

Related U.S. Application Data

(60) Provisional application No. 62/073,311, filed on Oct. 31, 2014, provisional application No. 62/149,903, (Continued)

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0064* (2013.01); *A61B 5/0077* (2013.01); *A61B 5/015* (2013.01);
(Continued)

(58) Field of Classification Search
CPC ..... A61B 5/055; A61B 5/7485; A61B 5/0064; A61B 5/0077; A61B 5/445; A61B 5/0033;
(Continued)

(56) References Cited

U.S. PATENT DOCUMENTS 5,309,921 A * 5/1994 Kisner ................ A61B 5/0064
128/925
5,492,122 A   2/1996 Button et al.
(Continued)

FOREIGN PATENT DOCUMENTS

JP    2010/278817 A    12/2010
WO    2005/063120 A1    7/2005

OTHER PUBLICATIONS

Steere, Anna, Battling Burns in MR, Health Imaging (Sep. 11, 2014), http://www.healthimaging.com/topics/practice/management/battling-burns-in-MR.
(Continued)

*Primary Examiner* — Amanda Lauritzen Moher
*Assistant Examiner* — Amy J Shafqat
(74) *Attorney, Agent, or Firm* — Warner Norcross + Judd LLP

(57) ABSTRACT

A system for monitoring a patient during MRI imaging to prevent patient burns. The system includes a barrel to provide an MRI image of a patient and an infrared camera to image the patient separately from the MRI image. The infrared camera includes an adjustable field of view and is positionable at a plurality of viewing angles relative to the
(Continued)

longitudinal axis of the barrel. The infrared camera is coupled to a processor adapted to monitor the surface temperature of the patient based on the output of the infrared camera. The processor is further adapted to control at least one of the field of view of the infrared camera and/or the viewing angle of the camera during MRI imaging of the patient. The system further includes a patient gown formed of an infrared transmissive material that provides visual concealment for the patient.

13 Claims, 19 Drawing Sheets

Related U.S. Application Data filed on Apr. 20, 2015, provisional application No. 62/208,070, filed on Aug. 21, 2015.

(51) Int. Cl.
*A61B 5/01* (2006.01)
*G01R 33/28* (2006.01)

(52) U.S. Cl.
CPC ............ *A61B 5/445* (2013.01); *A61B 5/7485* (2013.01); *G01R 33/283* (2013.01); *G01R 33/288* (2013.01)

(58) Field of Classification Search
CPC ............... A61B 5/0035; A61B 5/0046; A61B 2560/0242; A61B 2560/0266; A61B 5/0008; A61B 5/01–015; A61B 8/546; A61B 5/150954; A61B 5/02055; A61B 5/0878; A61B 2562/0271; A61B 2017/00084; A61B 1/128; A61B 2010/0019; A61B 2018/00714; A61B 2018/00791; A61B 2050/001; A61B 2017/00911; A61B 5/0055; A61B 5/0263; A61B 2090/374; A61B 2090/3954; A61B 1/04; A61B 2034/2057–2057; A61B 2090/371; G01R 33/288; G01R 33/283; G01K 2213/00; G01K 7/36; G01K 7/38; G01K 7/00; G01K 3/00; G01K 3/005; G01K 3/02; G01K 3/08; G01K 3/14; G01K 3/10; G01K 2003/145; G01J 2005/0077; G01J 2005/0092; G06T 2207/10028; G06T 2207/10048; G06T 2207/10088–10096; H04N 5/2251
See application file for complete search history.

(56) References Cited

U.S. PATENT DOCUMENTS

| | | | | |
|---|---|---|---|---|
| 5,730,134 A | * | 3/1998 | Dumoulin | ................ A61B 5/01 600/412 |
| 5,916,161 A | * | 6/1999 | Ishihara | ................. A61B 5/055 324/315 |
| 8,077,480 B2 | | 12/2011 | Ophoven et al. | |
| 8,190,243 B2 | | 5/2012 | Welches et al. | |
| 8,519,711 B2 | | 8/2013 | Sakakura | |
| 9,237,849 B1 | * | 1/2016 | McKenzie | .............. G06T 11/00 |
| 2001/0034891 A1 | * | 11/2001 | Matsushita | ........ A41D 13/1209 2/141.1 |
| 2004/0044271 A1 | | 3/2004 | Stone et al. | |
| 2007/0156021 A1 | | 7/2007 | Morse et al. | |
| 2007/0230767 A1 | | 10/2007 | Iwamatsu et al. | |
| 2007/0280508 A1 | | 12/2007 | Ernst et al. | |
| 2008/0000006 A1 | * | 1/2008 | Ochoa | ................ A41D 13/1236 2/114 |
| 2008/0275310 A1 | * | 11/2008 | Kim | ..................... A61B 5/4266 600/300 |
| 2009/0024023 A1 | * | 1/2009 | Welches | ............... A61B 18/201 600/424 |
| 2009/0105605 A1 | * | 4/2009 | Abreu | .................. A61B 5/0008 600/549 |
| 2010/0135550 A1 | * | 6/2010 | Arnon | .................... A61B 5/015 382/128 |
| 2010/0244833 A1 | * | 9/2010 | Sakakura | ................. G01K 7/36 324/309 |
| 2010/0245543 A1 | | 9/2010 | Greer et al. | |
| 2013/0093866 A1 | * | 4/2013 | Ohlhues | ................. A61B 5/055 348/65 |
| 2013/0116573 A1 | | 5/2013 | Herman | |
| 2013/0296709 A1 | * | 11/2013 | Zuzak | ................... A61B 5/0071 600/476 |
| 2013/0342851 A1 | * | 12/2013 | Dresel | .................... G01B 11/24 356/601 |
| 2014/0055133 A1 | * | 2/2014 | I | ............... G01R 33/28 324/309 |
| 2014/0148706 A1 | * | 5/2014 | Van Treeck | ............ A61B 5/015 600/474 |
| 2014/0249401 A1 | | 9/2014 | Van Den Brink et al. | |
| 2014/0276088 A1 | * | 9/2014 | Drucker | ................. A61B 5/489 600/473 |
| 2014/0350381 A1 | * | 11/2014 | Kim | ..................... A61B 5/7282 600/411 |
| 2015/0139515 A1 | * | 5/2015 | Smith | .................... A61B 6/032 382/131 |
| 2015/0224230 A1 | * | 8/2015 | Hirata | .................. A61N 5/0613 607/88 |
| 2015/0250388 A1 | * | 9/2015 | Arbabian | ............. A61B 8/0833 600/424 |
| 2015/0297311 A1 | * | 10/2015 | Tesar | ..................... G02B 21/16 600/411 |
| 2016/0035093 A1 | * | 2/2016 | Kateb | .................... G02B 23/24 382/131 |
| 2016/0073962 A1 | * | 3/2016 | Yu | .......................... A61B 5/721 600/407 |
| 2017/0110887 A1 | * | 4/2017 | Bell | ...................... H04B 5/0037 |
| 2018/0250072 A1 | * | 9/2018 | Rogers | ................ A61N 5/0625 |

OTHER PUBLICATIONS

International Search Report and Written Opinion of WO/2016/069967 dated May 17, 2016, 12 pages.

* cited by examiner

| EFL | 50mm |
|---|---|
| F/# | 1.2 |
| DETECTOR | FLIR A65 |
| PIXEL RESOLUTION | 640 X 512 |
| PIXEL PITCH | 0.017mm |
| FPA ACTIVE AREA | 10.880mm X 8.70mm |
| FOV | 12.4° X 9.9° |
| MINI FOCUS DIST. | 1.5m |
| HYPERFOCAL DIST. | 71m |
| HYPERFOCAL DEPTH OF FIELD | 36m |
| LENGTH | 50mm |
| DIAMETER | 58mm |
| WEIGHT | 280g |

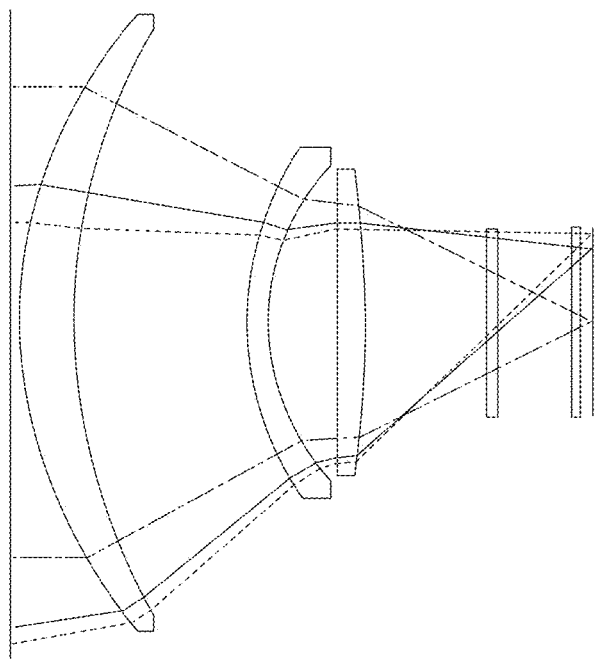

GENERAL LENS DATA:

| | | | |
|---|---|---|---|
| SURFACES: | 14 | LENS UNITS: MILLIMETERS | |
| STOP: | 9 | ANGULAR MAGNIFICATION: 2.833 | |
| TEMPERATURE (C) | 2.00000E+001 | FIELDS: 3 | |
| PRESSURE (ATM) | 1.00000E+000 | FIELD TYPE: ANGLE IN DEGREES | |
| EFFECTIVE FOCAL LENGTH: | 50 | Y-VALUE | WEIGHT |
| BACK FOCAL LENGTH: | 1.062 | 1  0.000000 | 4.000000 |
| TOTAL TRACK: | 57.53 | 2  7.983005 | 3.000000 |
| IMAGE SPACE F/#: | 1.092 | 3  9.978757 | 0.500000 |
| WORKING F/#: | 1.201 | WAVELENGTHS: 6 | |
| IMAGE SPACE NA: | 0.416 | UNITS: μm | |
| STOP RADIUS: | 8.075 # | VALUE | WEIGHT |
| PARAXIAL IMAGE HEIGHT: | 8.797 | 1  8.000000 | 0.880000 |
| ENTRANCE PUPIL DIA: | 63.178 | 2  9.000000 | 0.990000 |
| ENTRANCE PUPIL POSITION: | 45.75 | 3  10.000000 | 1.000000 |
| EXIT PUPIL DIA: | 99.53 | 4  11.000000 | 0.970000 |
| EXIT PUPIL POSITION: | -17.720 | 5  12.000000 | 0.850000 |
| FIELD TYPE: ANGLE IN DEGREES | | 6  13.000000 | 0.660000 |
| MAXIMUM RADIAL FIELD | 9.979 | | |
| PRIMARY WAVELENGTH | 10μm | | |

Fig. 14

MAGNETIC RESONANCE IMAGING PATIENT TEMPERATURE MONITORING SYSTEM AND RELATED METHODS

BACKGROUND OF THE INVENTION

The present invention relates to magnetic resonance imaging procedures, and more particularly to systems and methods to measure and/or monitor patient temperature during such procedures to prevent burns.

Magnetic residence imaging (MRI) is used to image a patient's internal organs, tissue and in some cases bone. During an MRI, radio-frequency (RF) energy is transmitted through the patient. It has been discovered that RF energy absorption by the patient, implanted or nearby medical devices, and/or MRI ground loops, routinely lead to heating of the patient's skin surfaces in localized or widespread areas. In some cases, the heating leads to RF burns on the patients. Those burns can be first, second or third degree burns in extreme cases.

There are several reports indicating that the limbs or body parts of MRI burn patients were in direct contact with RF body coils or other RF transmitting coils of the MRI equipment. In other cases, it is suspected that the patient contacted an exterior conductive element, such as clothing, or other parts of the MRI equipment. In further MRI burn cases, it is suspected that there was skin-to-skin contact points, caused by the patient placing their thumbs on their thighs, midsection or other areas where RF energy is concentrated during an MR scan.

According to another report, a Joint Commission Sentinel Event Alert, which cited the Manufacture and User Facility Device Experience database of the FDA, "70% of MRI complications are related to thermal burns. 'The single most common and adverse event in the MRI environment reported to the FDA is that of MRI burns,' says Emanuel Kanal, MD, FACR, FISMRM, AANG of the University of Pittsburgh Medical Center in Pennsylvania." Steere, Anna, *Battling Burns in the MR*, www.healthimaging.com, Sep. 11, 2014. This report also recognized that there are multiple causes of MRI burns. For example, RF energy might not deposit uniformly throughout the patient's body. In some cases, blood flow can redistribute the RF energy resulting in non-uniform, in vivo temperatures. Certain in vivo regions can become more heated than others, and temperatures increase thereby causing RF burns.

Thus, there remains room for improvement in the field of reducing burns to patients undergoing MRI procedures.

SUMMARY OF THE INVENTION

A system and method that utilizes a thermal imaging device to measure and monitor a patient's temperature during an MRI procedure to prevent adverse events, such as burns on the patient's skin surface, are provided.

In one embodiment, the system includes an MRI equipment barrel to provide an MRI image of a patient, and an infrared camera to image the patient separately from the MRI image. The infrared camera includes one or more adjustable parameters. The adjustable parameters can include at least one of an adjustable field of view, an adjustable lens tilt angle, and an adjustable viewing angle. The system further includes a processor that monitors the surface and/or subdermal temperature of the patient based on the output of the infrared camera.

In another embodiment, the processor controls the tilt angle of the infrared camera lens. Controlling the tilt angle of the infrared camera lens includes tilting the optical axis of the camera lens. Stated somewhat differently, controlling the tilt angle of the infrared camera lens includes rotation of a lens plane relative to an image plane. Controlling the tilt angle of the infrared camera lens can improve infrared image acquisition within the barrel.

In yet another embodiment, the processor controls at least one of the field of view of the infrared camera and the viewing angle of the camera during MRI imaging of the patient. In still another embodiment, the system can include a patient gown formed of an infrared transmissive material that provides visual concealment for the patient. The gown, in turn, facilitates thermal monitoring of the patient's skin surface, yet still provides the patient some privacy. The infrared transmissive material can include a polymer, for example polypropylene, polyethylene, and combinations of the same. The infrared transmissive material can include microperforations to provide breathability in some embodiments.

In even another embodiment, the infrared camera can be positioned outside of an MRI magnetic field to minimize electrical interference to or from the infrared camera. Such placement also can minimize the noise detected by the infrared camera, thus providing more detailed, accurate temperature scanning of the patient's skin surface. To further minimize electromagnetic interference, data cables and power cables can include shielding. The data cables and the power cables can additionally include a low pass filter to attenuate noise which might otherwise interfere with MRI imaging. Interference or noise from the infrared camera can also be reduced by enclosing the infrared camera in a Faraday cage. The Faraday cage can include an enclosure of conductive material, for example aluminum, to minimize degradation of the MRI image due to infrared camera electromagnetic radiation.

In a further embodiment, a method of performing an MRI without burning a patient is provided. The method generally includes positioning an infrared camera in a plane generally parallel with the central axis of an MRI barrel. The method further includes monitoring, using the infrared camera, the temperature of the patient's skin and optionally subdermal temperatures during MRI imaging, and altering, during the MRI imaging, at least one of the camera field of view, the camera lens tilt angle, and the camera viewing angle to scan the patient substantially from head to toe within the MRI barrel. The method further includes correlating surface temperatures with internal body temperatures during MRI imaging, and substantially in real time.

In still a further embodiment, the camera field of view, the camera lens tilt angle, and/or the camera viewing angle are further varied in response to a detection of a localized hot spot on the patient. The MRI is paused or terminated in response to the temperature of the patient's body exceeding a threshold temperature associated with possible RF burns. The method can further include donning the patient with a privacy gown that allows infrared wavelengths to pass therethrough, while also providing visual concealment for the patient's body. The privacy gown can be formed of a polymer, for example polyethylene or polypropylene, optionally having micro-perforations formed therein.

The system and method of the current embodiments therefore provide improved detection of RF burns during MRI imaging, including wide-area scans and small-area scans of adult patients, adolescent patients, and pediatric patients. By detecting an increase in skin surface temperature and/or subdermal temperatures of the patient with thermal imaging, the current embodiments can reduce the incidence of RF burns while maintain patient privacy and not otherwise interfering with MRI procedures.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 14 is a ray trace model of a tilt lens for the infrared camera of FIG. 13.

DESCRIPTION OF THE CURRENT EMBODIMENTS

The current embodiments generally relate to a system and a method that utilizes a thermal imaging device to measure and monitor a patient's temperature and/or other thermally related characteristics during an MRI procedure to prevent adverse events. The monitored temperature can be the temperature of the patient's skin, subdermal tissue, and/or internal organs or other structure.

Figure 1:
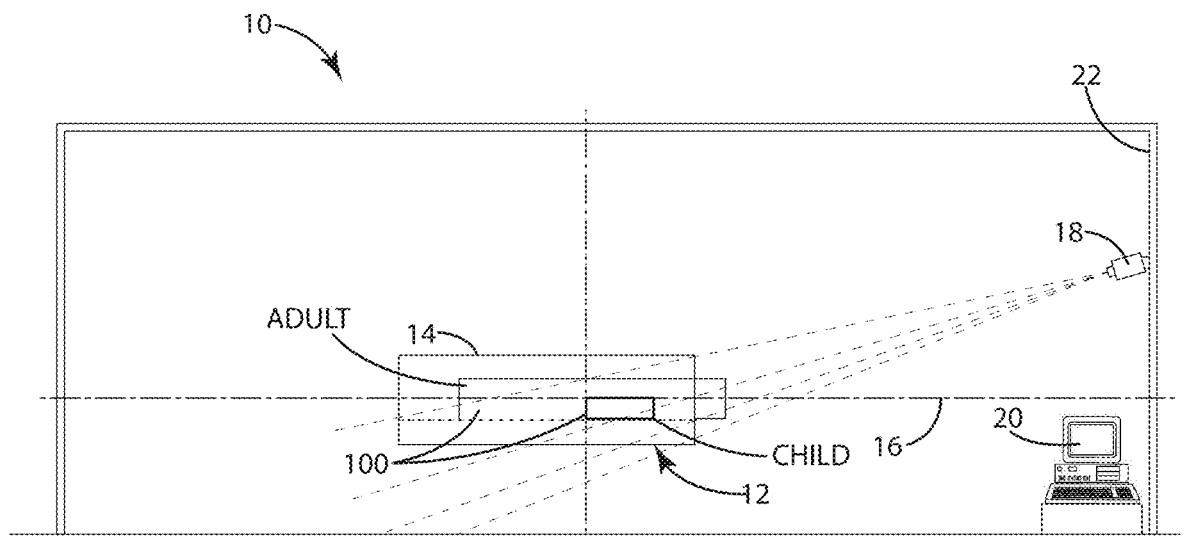
FIG. 1 is a side view of an MRI procedure room layout including a system for monitoring a patient undergoing an MRI in accordance with a current embodiment.

Referring now to FIG. 1, a system for measuring and monitoring a patient's temperature is illustrated and generally designated 10. The system 10 generally includes a MRI machine 12 to provide an MRI image of a patient 100, the MRI machine 12 including a barrel 14 defining a longitudinal axis 16. The system 10 additionally can include a thermal imaging device 18 having an adjustable field of view and/or that is positionable at a plurality of viewing angles as shown, relative to the longitudinal axis 16. The system 10 can include a processor 20 adapted to monitor the patient's skin surface and/or subdermal temperature based on the output of the thermal imaging device 18. Although illustrated as located in the same room as the MRI machine 12, the processor 20 can be located in a separate room to reduce interference between the MRI machine 12 and the processor 20. As explained below, the processor 20 can control the field of view of the thermal imaging device 18, the viewing angle of the thermal imaging device 18, the lens tilt angle of the thermal imaging device 18, and/or other parameters, to provide improved observation at various locations within the barrel of the MRI machine 12.

More particularly, the thermal imaging device 18 can include an infrared camera optionally mounted to a wall 22 of an MRI imaging room. The infrared camera can be selected to include a thermal detection range that encompasses the expected patient skin surface temperature. One suitable infrared camera is an A65 thermal imaging camera from FLIR Systems, Inc. of Wilsonville, Oreg., having a detection range of between −40° C. to 160° C. Other infrared cameras can be used in other embodiments as desired.

Figure 2:
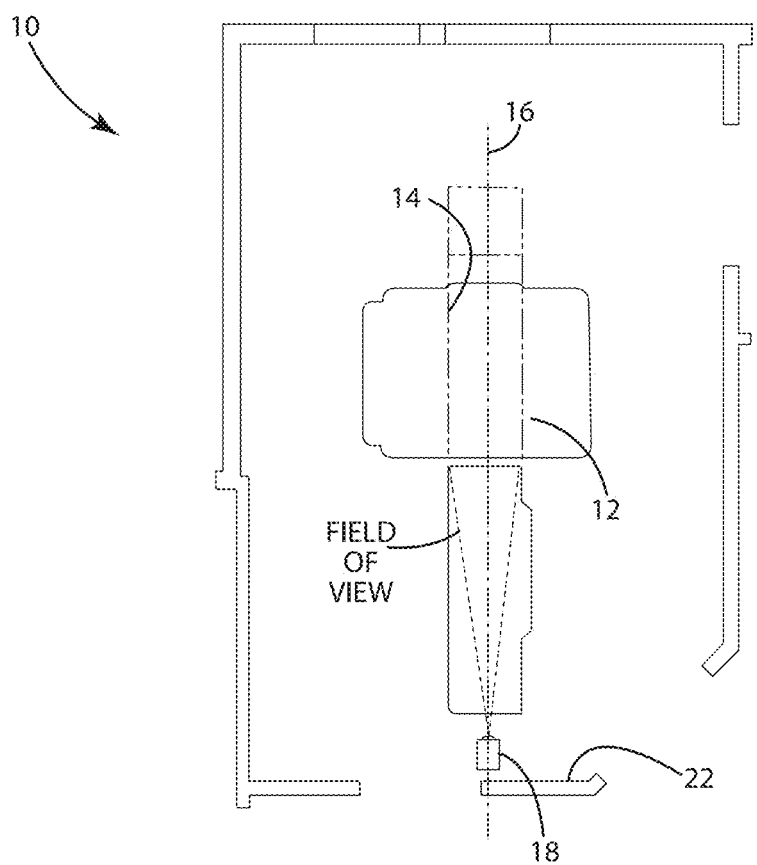
FIG. 2 is a top view of the MRI procedure room layout including the system in accordance with the current embodiment.
Figure 3:
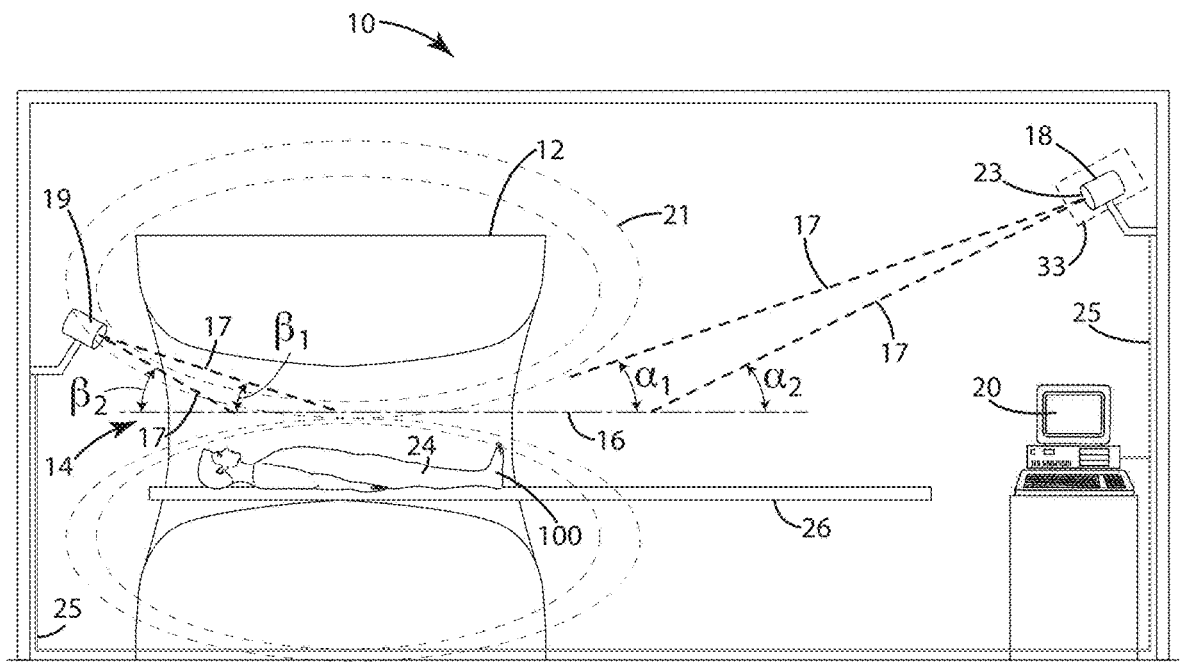
FIG. 3 is a side view of an MRI procedure room layout further illustrating multiple viewing angles associated with multiple infrared cameras when monitoring a patient undergoing an MRI.

The infrared camera 18 is offset at a preselected angle relative to the central axis 16 of the MRI barrel 14. The preselected angle, or viewing angle, is shown in FIG. 3 and denoted $\alpha_1$, $\alpha_2$, $\beta_1$ or $\beta_2$, defined by the angle between the central axis 16 of the MRI barrel and the camera line of sight 17. The viewing angle can be selected based on the dimensions of the patient, and can differ among adult patients, adolescent patients, and pediatric patients. The infrared camera 18 is optionally aligned with a plane defined by the central axis 16 seen in the top plan view of FIG. 2. In this manner, the infrared camera 18 can collect images of the patient's body 100 while the patient is in the barrel of the MRI machine 12, whether an adult body or child body. Where two infrared cameras are utilized, a second infrared camera 19 can be positioned to view the barrel 14 from the opposing side of the MRI machine 12. The first and/or second camera 18, 19 can be laterally offset from the central axis 16, being outside of the plane that bisects the MRI machine 12. In addition, the first camera 18 is depicted as being substantially outside of the magnetic field 21 associated with the MRI machine 12, while the second camera 19 is depicted as being within or partially within magnetic field 21 associated with the MRI machine 12. The cameras 18, 19 optionally includes electromagnetic shielding for example a Faraday cage (discussed below) to reduce interference between the cameras 18, 19 and the MRI machine 12 during MRI imaging.

The infrared camera 18 can include a tilt angle lens 23, which can be controlled to improve the focus of the infrared camera 18 within the barrel 14. Controlling the tilt angle of the lens 23 includes tilting the optical axis of the lens 23. Stated somewhat differently, controlling the tilt angle of the lens 23 includes rotation of a lens plane relative to an image plane. By controlling the tilt angle, the camera viewing angle can remain fixed. In other embodiments however both the lens tilt angle the camera viewing angle are varied to provide improved focus on the patient 100 during MRI imaging. The camera lens 23 can additionally shift relative to the image plane, alone or in combination with the tilting of the camera lens 23 relative to the image plane.

The infrared camera 18 tilt angle lens 23 can also provide a greater depth of focus and improved thermal accuracy and imaging. As shown in FIG. 1, the infrared camera 18 can operate through 5°, 8° and 10° at different fields of view. Of course, other angles can be selected as desired. This can enable the infrared camera 18 to view or scan the entire body of the patient substantially from head to toe while in the MRI barrel 14. As noted above, the infrared camera 18 alternatively or additionally utilizes a varying viewing angle so that it can collect images of the entire body 100. By varying the viewing angle, the infrared camera 18 can collect images of the patient even though the IR camera 18 is not aligned with the central axis 16.

Figure 6:
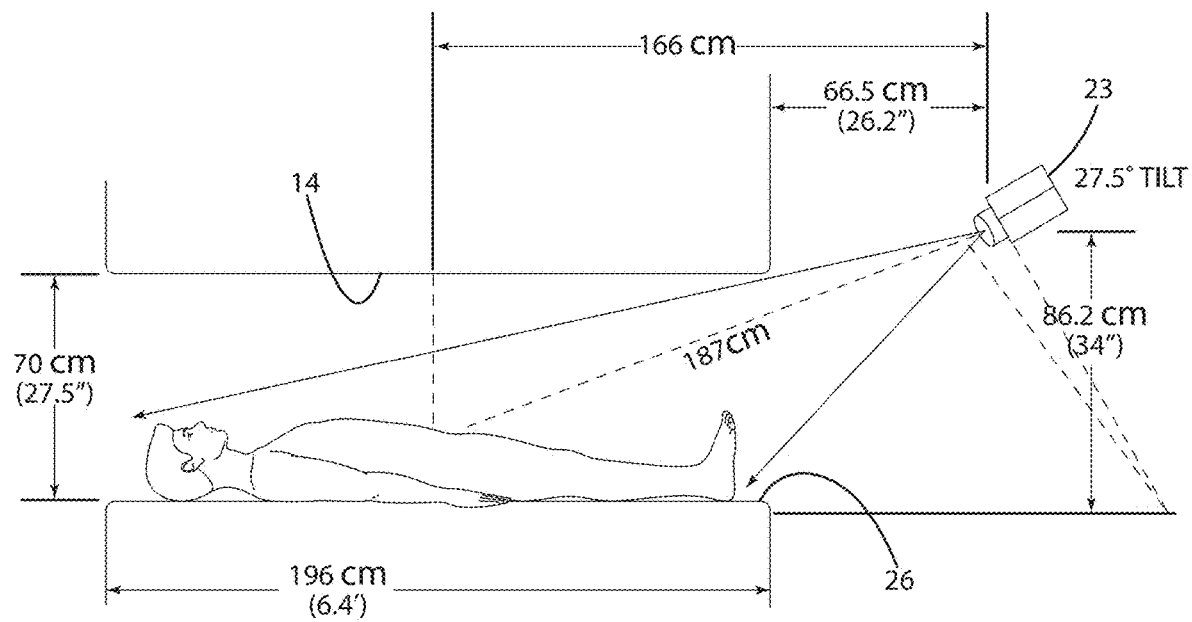
FIG. 6 is a side view of an MRI procedure room layout illustrating an infrared camera without a tilt lens.
Figure 7:
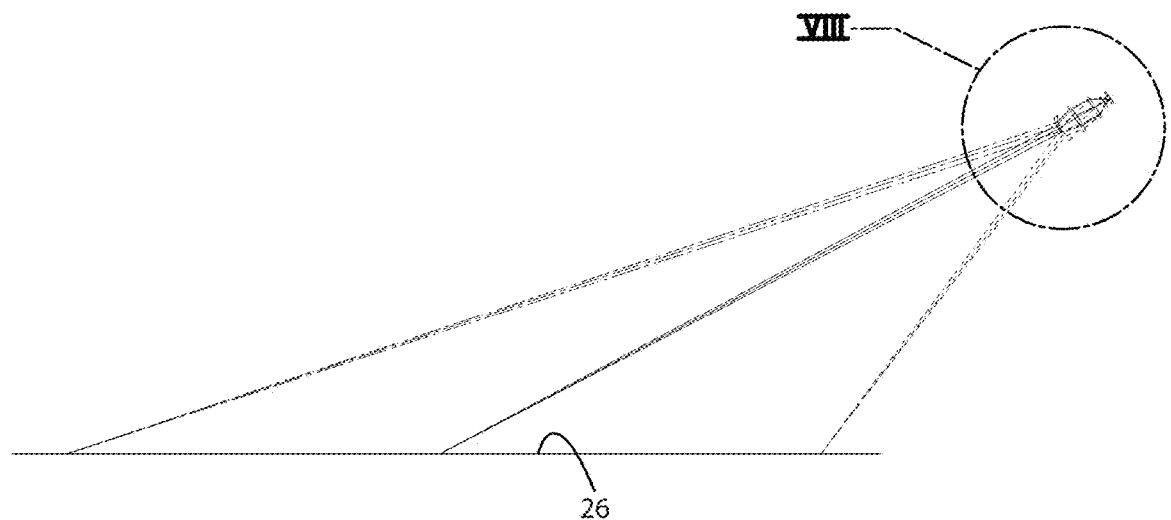
FIG. 7 is a ray trace model of the infrared camera of FIG. 6.
Figure 8:
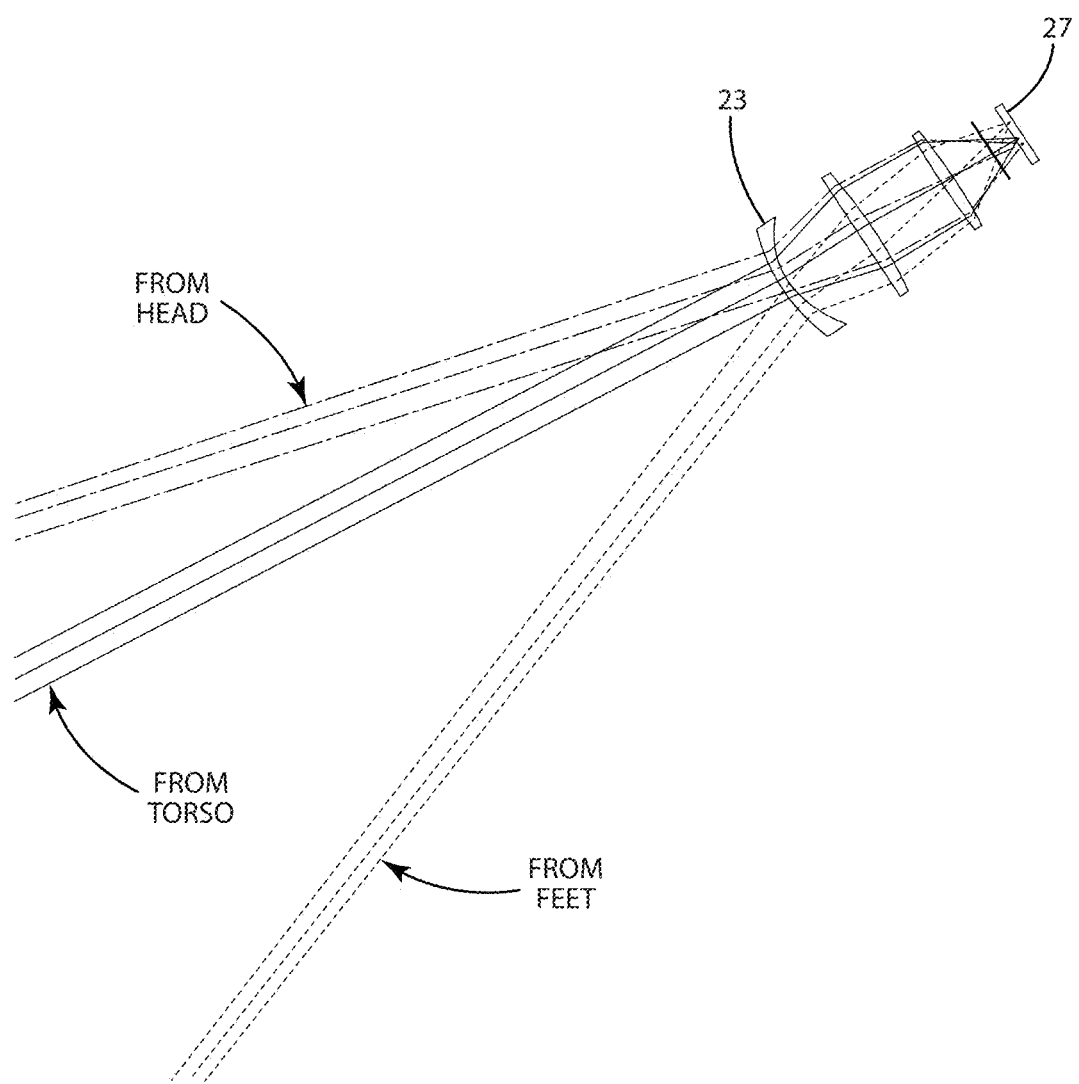
FIG. 8 is a close-up of the ray trace model in region VIII of FIG. 7.
Figure 9:
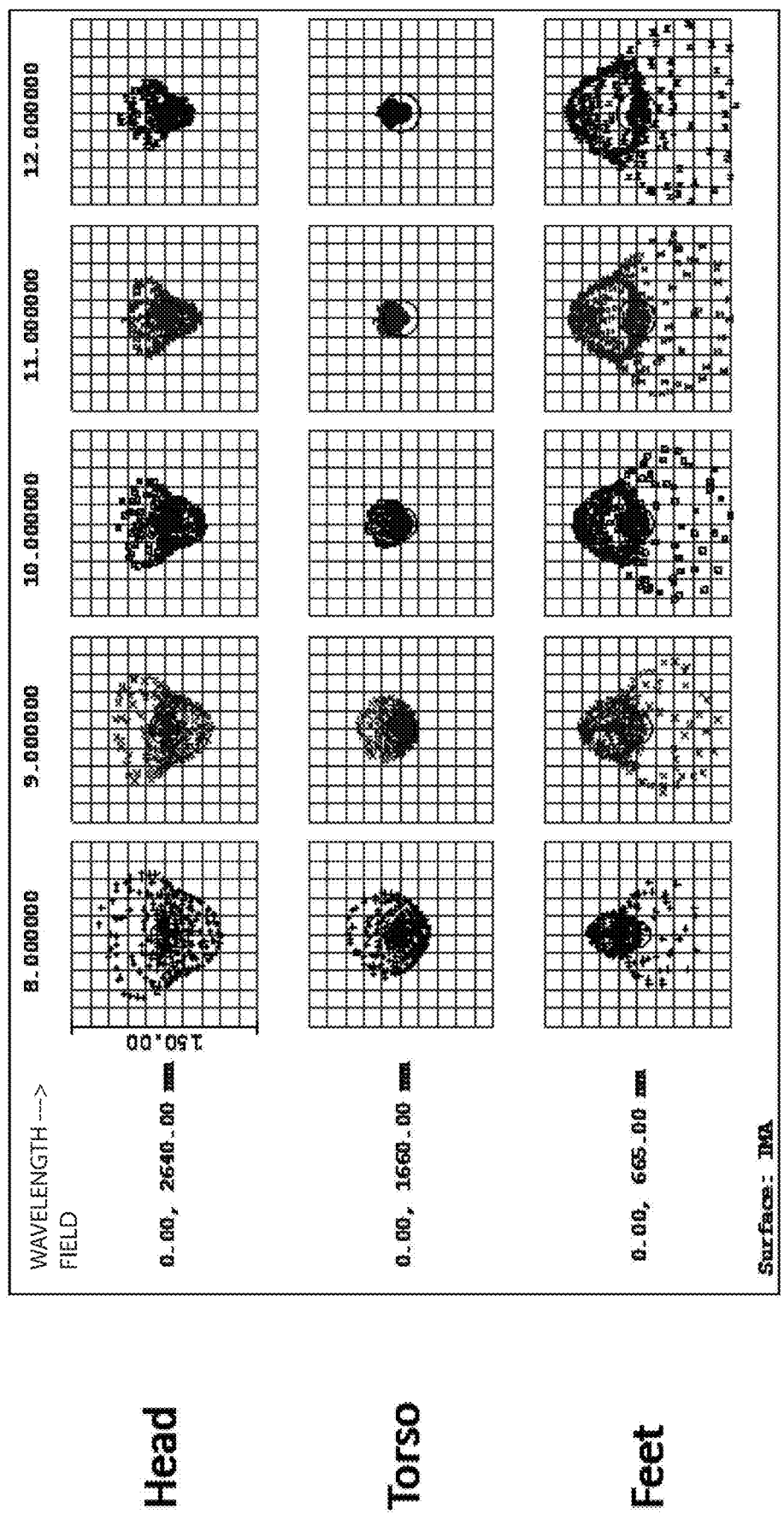
FIG. 9 are geometrical spot diagrams of the ray trace model of FIG. 7, illustrating the center of the field of view in sharp focus and the periphery of the field of view out of focus.
Figure 10:
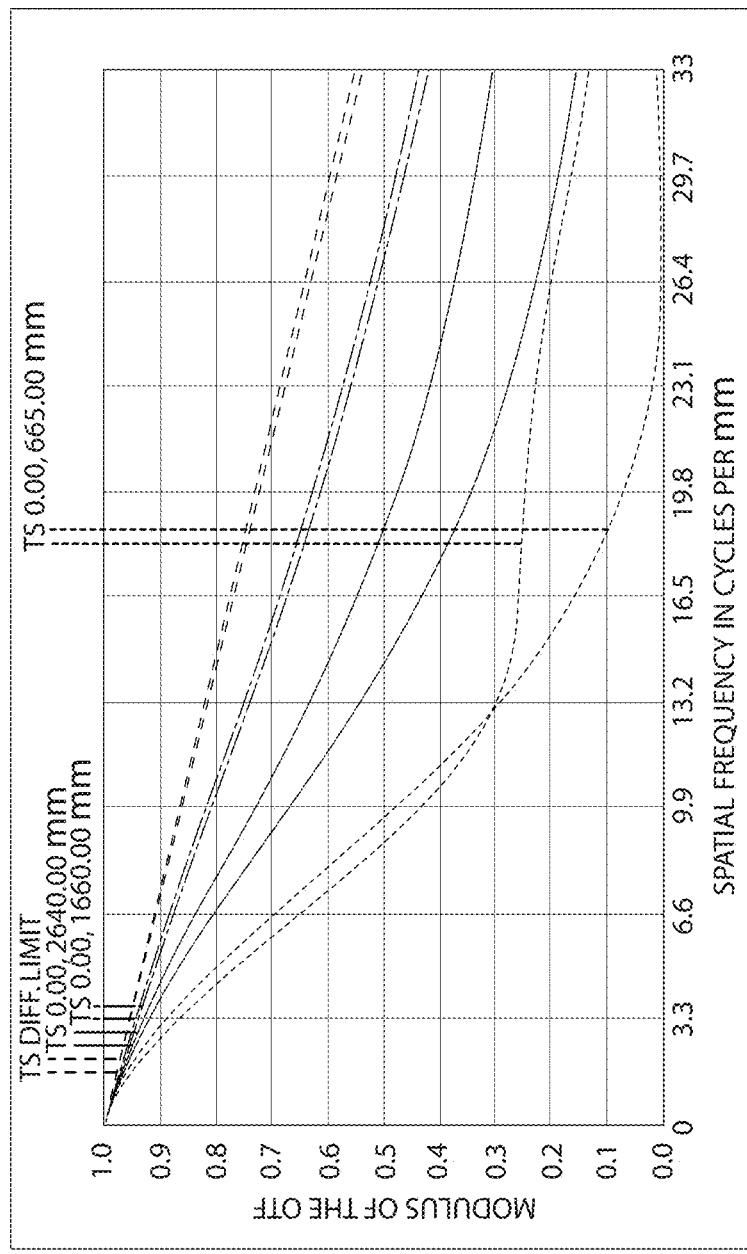
FIG. 10 is graph illustrating the modulation transfer function for the ray trace model of FIG. 7, illustrating poor contrast over the field of view.

FIGS. 6-8 illustrate an MRI barrel 14 within the infrared camera field of view, the infrared camera 18 lacking a tilt lens. As discussed below, the absence of a tilt lens can leave the thermal image out of focus at the patient's head and at the patient's feet. Referring again to FIG. 6, the infrared camera 18 is vertically offset from the patient tray 26 by distance of 86.2 cm, horizontally offset from the feet by 66.5 cm, horizontally offset from the torso by 166 cm, and horizontally offset from the head by 262.5 cm. FIGS. 7-8 depict the ray trace from the patient's head, the patient's torso, and the patient's feet through the camera lens, ultimately impinging the photo-sensor image plane 27. Geometric spot diagrams (FIG. 9) show that only the center of the field of view is in sharp focus, namely the torso, while the head and the feet remain out of focus. Similarly, FIG. 10 illustrates the modulation transfer function (MTF) showing a poor contrast for the patient's head and the patient's feet.

Figure 11:
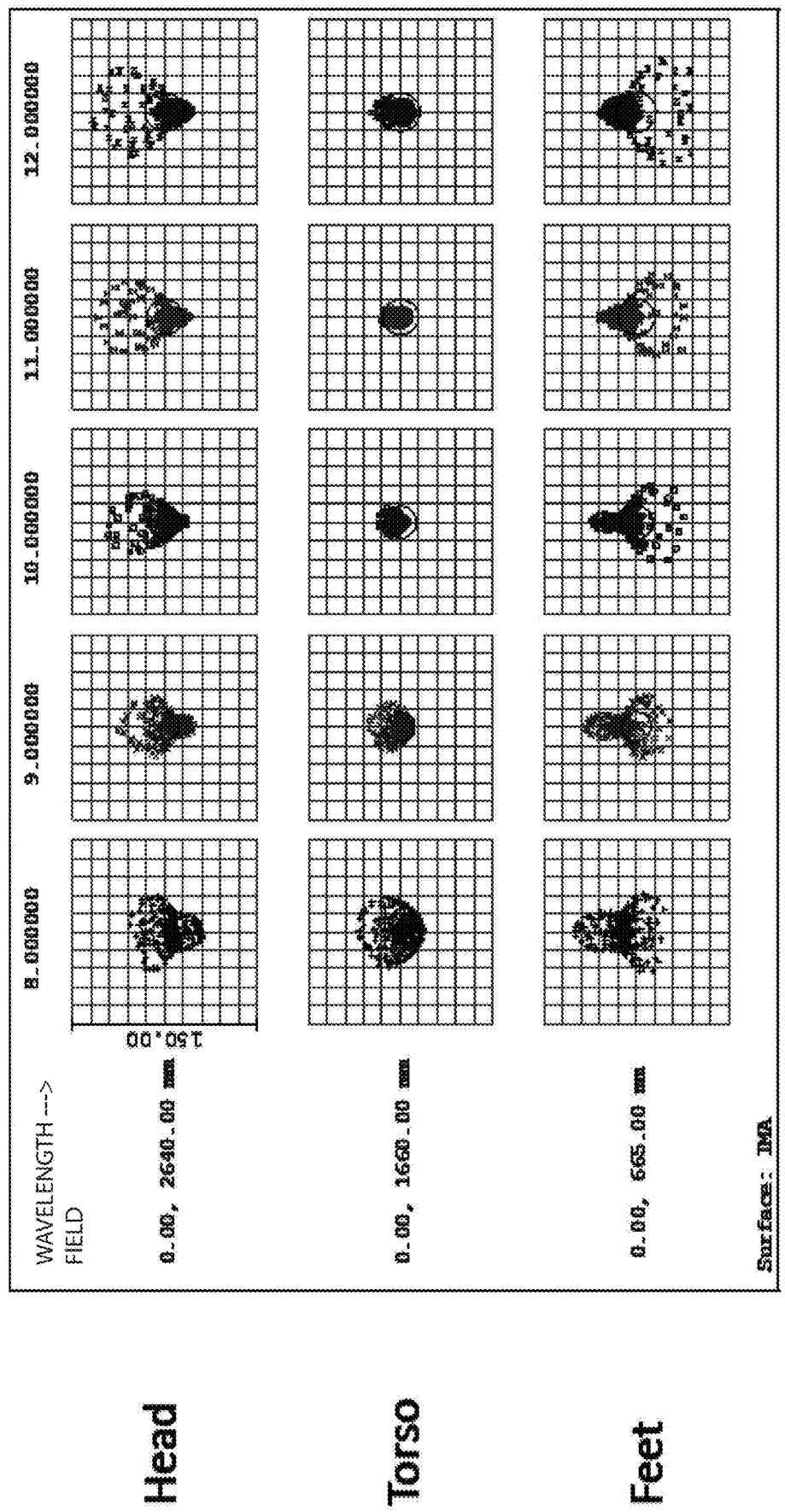
FIG. 11 are geometrical spot diagrams of a ray trace model for an infrared camera including a tilt lens, illustrating the center and periphery of the field of view in focus.
Figure 12:
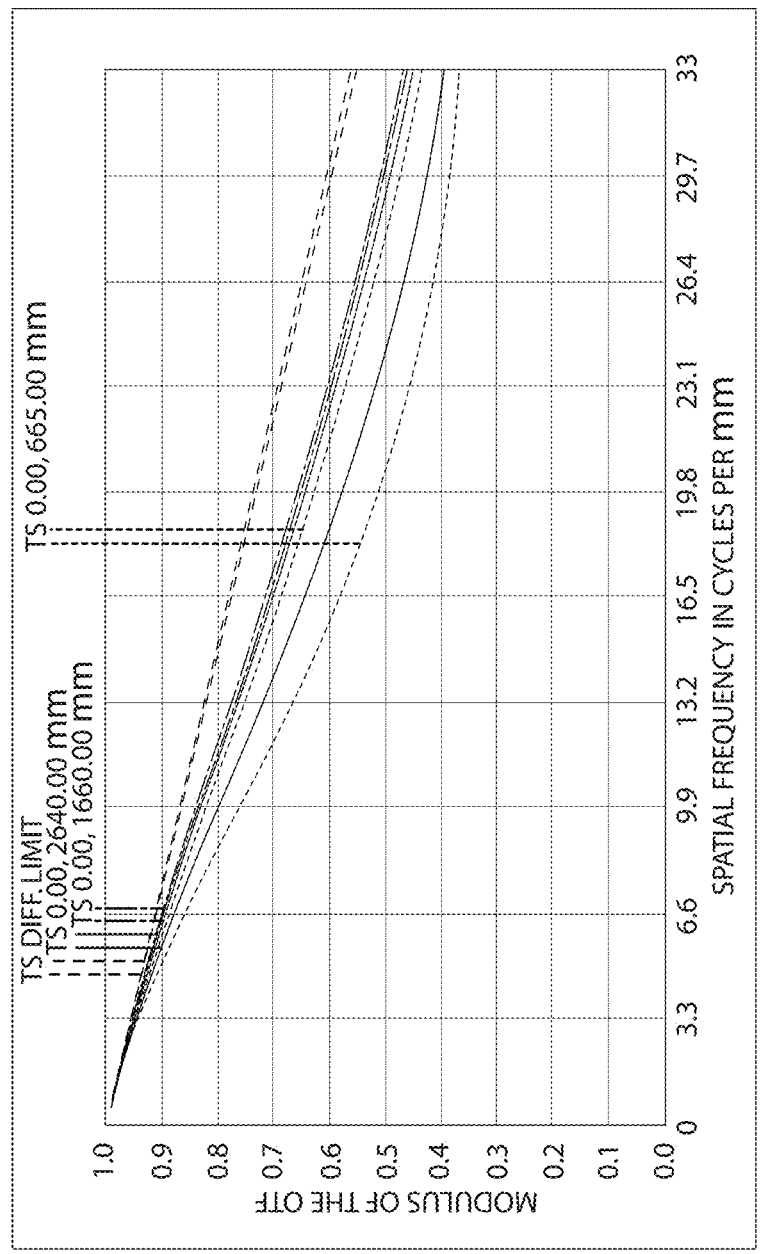
FIG. 12 is a graph illustrating the modulation transfer function for a ray trace model including a tilt lens, illustrating good contrast over the field of view.

When the camera 23 of FIG. 6 is modified to include a tilt lens, however, the focus of the thermal image improves at the patient's feet and the patient's head. As shown in FIG. 11 for example, the geometric spot diagrams illustrate uniformity over the entire field of view of the infrared camera 23. FIG. 12 also illustrates the MTF for the patient's head, torso, and feet, showing good contrast at each location within the field of view.

As generally shown in FIG. 3, the system also can include an infrared transmissive privacy gown 24 that the patient 100 dons before undergoing the MRI procedure. The privacy gown 24 is transmissive in the infrared long-wave and/or mid-wave infrared spectrum, for example, 8 to 14 microns and/or 2 to 5 microns, respectively, while being opaque to visible light. The privacy gown 24 can be transmissive due to an open weave structure or fabric that allows the infrared wavelengths to penetrate the privacy gown 24 while still concealing the patient from the view of others. Alternatively, the privacy gown 24 can be transmissive to infrared light by constructing the gown 24 from plastic or films that allow infrared wavelength transmission. For example, the privacy gown can be formed from a polymer film or a polymer textile, optionally polyethylene or polypropylene. The polymer textile can have an open structure, optionally knitted and further optionally woven. Further by example, the privacy gown 24 can include microperforations or slits to provide improved breathability and/or infrared imaging, while in other embodiments the privacy gown 24 is substantially non-porous.

To further minimize electromagnetic interference, data cables and power cables extending to and from the cameras 18, 19 can include shielding. For example, data cables 25 extending to the infrared cameras 18, 19 can include shielding to reduce electromagnetic noise from affecting the data signals therein, and power cables 25 extending to the infrared camera can include shielding to reduce electromagnetic radiation from interfering with the MRI machine 12. The cables 25 can additionally include a low pass filter to attenuate noise which might otherwise interfere with MRI imaging. The low pass filter is optionally an inductor to block high frequency signals in the power cables and/or the data cables, where the high frequency signals might otherwise interfere with operation of the MRI machine 12.

Figure 23:
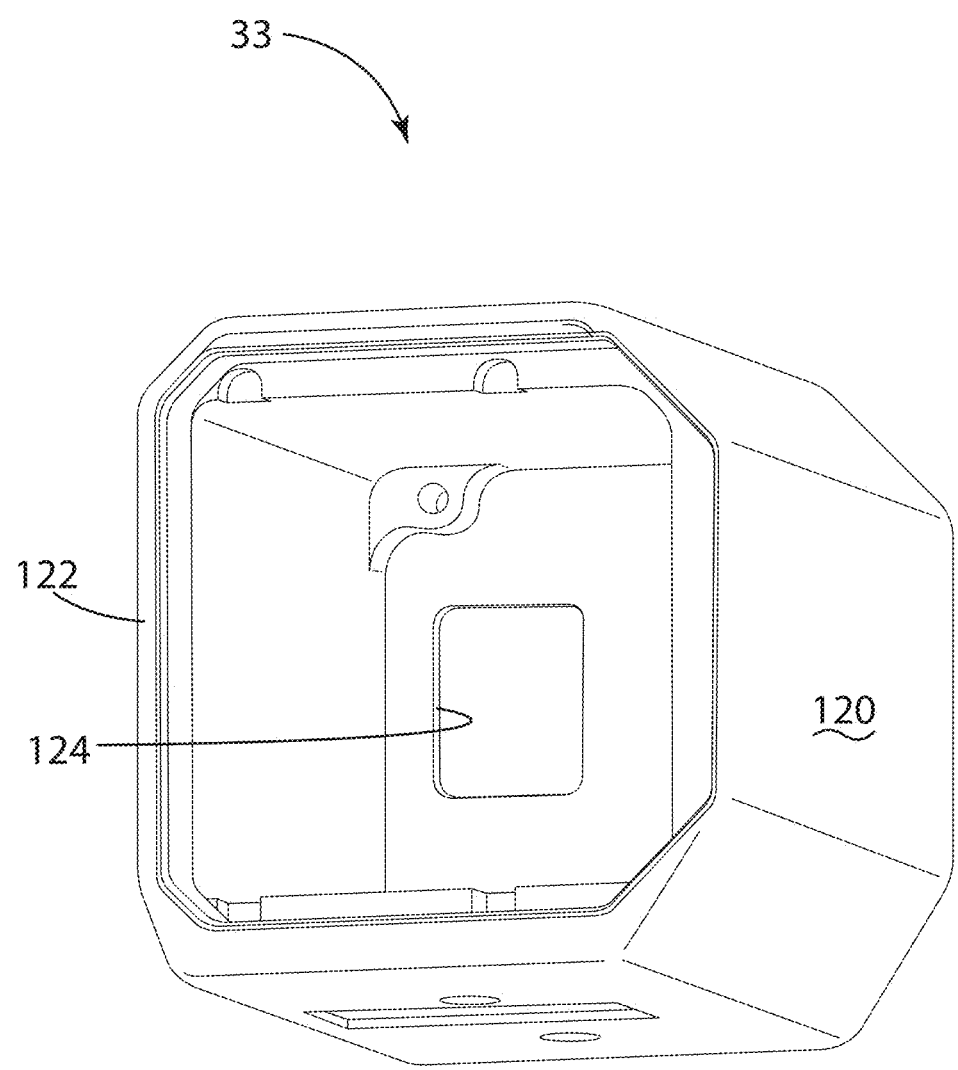
FIG. 23 is a perspective view of the Faraday cage of FIG. 22.

One or both infrared cameras 18, 19 can include a Faraday cage 33. The Faraday cage 33 can include an enclosure of conductive material, the enclosure being a complete enclosure or a partial enclosure. The enclosure of conductive material can reduce degradation of the MRI image due to electromagnetic radiation from the infrared camera 18, 19 and can reduce degradation of the infrared camera output due to electromagnetic radiation from the MRI machine 12. The enclosure defines an interior volume for all or a portion of the infrared camera 18, 19. As shown in FIG. 23, a five-sided enclosure 120 includes a primary opening 122 aligned with the camera lens 29 to provide an optical path for the infrared camera 18, 19. The enclosure 120 can include a thermal imaging array therein, for example a 640×512 thermal imaging array for the Tau 640 by FLIR Systems, Inc. The thermal imaging array 31 (shown in FIG. 13) is entirely recessed within the interior volume of the enclosure 120, and the lens 29 protrudes from or is supported externally of the primary opening 122. The enclosure 120 includes a secondary opening 124 to allow a transmission line therethrough, the transmission line being electrically connected to the infrared camera 18 for the transmission of power, data, or both power and data. In the present embodiment, the enclosure 120 is formed from aluminum, while in other embodiments the enclosure is formed form copper. The enclosure 120 is a conductive mesh in some embodiments, while in other embodiments the enclosure 120 is non-perforated. Electromagnetic interference (EMI) gaskets and overlapping joints further seal the thermal imaging array 31 within the enclosure 120.

As noted above, the infrared camera 18 is associated with a processor 20. The processor 20 includes computer readable instructions that, when executed, cause the processor 20 to perform certain method steps based on the output of the IR camera 18. In general terms, the methods steps can include capturing a thermographic image or related data of the patient's surface temperature or subdermal temperature to be displayed to the MRI operator, generating a computer model of the patient's surface temperature, comparing the computer model of the patient's surface temperature or subdermal temperature against one or more threshold values that are indicative of an unsafe skin condition (e.g., an irritation, or a first, second or third degree burn), signaling the unsafe skin condition to the MRI operator, causing the MRI machine to pause or terminate MRI imaging, adjusting the viewing angle of the infrared camera 18, adjusting the field of view of infrared camera 18, adjusting the lens tilt angle of the infrared camera 18, adjusting the scanning frequency of the infrared camera 18, and/or differentiating various thermal conditions in the computer model to identify air pockets beneath the gown 24.

Figure 4:
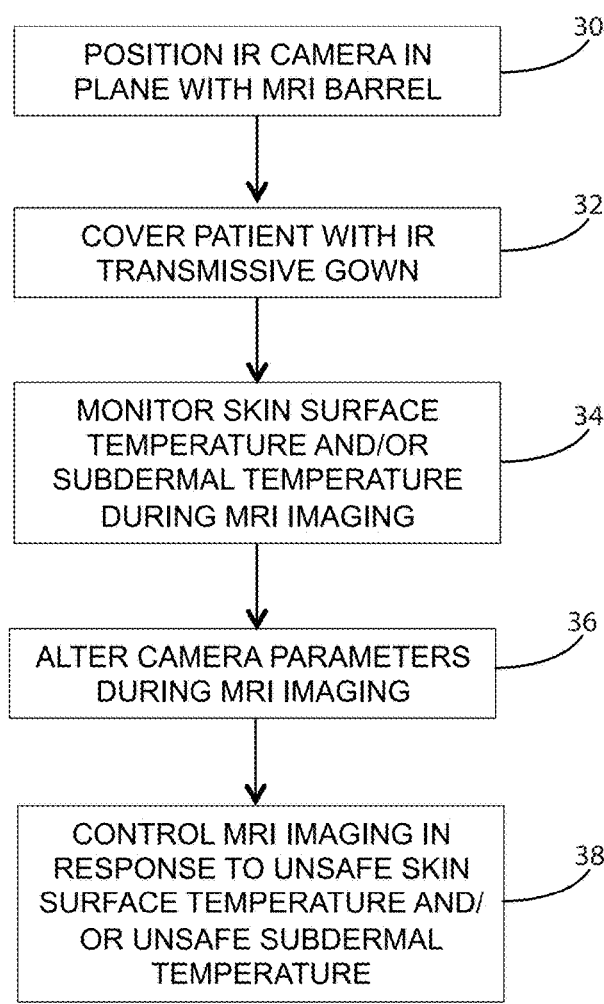
FIG. 4 is a flow chart for a method of monitoring a patient undergoing an MRI in accordance with a current embodiment.

The above processing steps are presented in greater detail in connection with the flow chart of FIG. 4. In particular, the flow chart of FIG. 4 includes a method of performing MRI imaging without burning a patient with associated RF energy, the method including: (a) positioning an infrared camera in a plane generally parallel with the central axis of an MRI barrel, (b) donning a patient with an infrared transmissive privacy gown, (c) monitoring the patient's skin surface temperature during MRI imaging, (d) altering the field of view of the infrared camera, the lens tilt angle of the infrared camera, and/or the viewing angle of the infrared camera to evaluate for unsafe skin surface temperatures during MRI imaging, (e) controlling MRI imaging in response to an unsafe skin surface or subdermal temperature.

Positioning an infrared camera in a plane generally parallel with the central axis of an MRI barrel is depicted as step 30 in FIG. 4. As shown in FIGS. 1 and 3, the infrared camera 18 is horizontally offset from the MRI machine 12 and vertically offset from the barrel central axis 16. Where two infrared cameras are utilized, a second infrared camera 19 can be positioned to view the barrel 14 from the opposing side of the MRI machine 12. Additional infrared cameras can be positioned at various locations relative to the MRI barrel. In the illustrated embodiment, the plane encompasses the central axis 16 of the MRI barrel and extends vertically, bisecting the MRI machine.

Donning a patient with an infrared transmissive privacy gown is depicted as step 32 in FIG. 4. This step generally includes providing a privacy gown 24 that is transmissive to infrared light. The privacy gown 24 can be formed of a fabric having a pre-selected porosity or openness and thickness. For example, the privacy gown 24 can be formed of a fabric having an open weave structure, for example a single layer acrylic, polyester and/or cotton fabric. The privacy gown 24 is generally transmissive to RF energy in the long-wave infrared spectrum, for example 8 microns to 14 microns, and/or the mid-wave infrared spectrum, for example 2 microns to 5 microns. However, the privacy gown also conceals the skin of the patient from observers standing nearby.

Monitoring the skin surface temperature and/or subdermal temperature during MRI imaging is depicted as step 34 in FIG. 4. This step generally includes evaluating the output of the infrared camera 18 (or cameras 18, 19) as the patient undergoes MRI imaging. During MRI imaging, the patient is typically in the supine position on a patient tray 26. The MRI machine 12 uses radio waves and a magnetic field to generate images for processing by a computer, optionally the processor 20. Throughout MRI imaging, the processor 20 can evaluate the output of the infrared camera 18 (or cameras 18, 19) to determine the patient's surface temperature through the privacy gown 24. For example, the processor 20 can generate a two-dimensional or three-dimensional computer model of the patient's surface temperature and/or subdermal temperature for comparison against a threshold value of the same. Also by example, the processor 20 can correlate surface temperatures with internal body temperatures, substantially in real time. If the patient's surface, subdermal or internal body temperature exceeds the threshold value at any point on the computer model, the processor 20 can cause the MRI machine 12 to reduce or terminate the application of RF energy to the patient 100. If the privacy gown 24 is not transmissive to infrared wavelengths, the processor 20 can instead can generate a two-dimensional or three-dimensional computer model of the gown's temperature for comparison against a threshold value of the same, potentially revealing the temperature of the underlying skin areas.

Monitoring the skin surface and/or subdermal temperature during MRI imaging can also include differentiating various conditions of thermal imaging detected on the patient. For example, air pockets or other areas can be formed adjacent the patient's body, creases and folds in the fabric can sometimes can create "cool spots" that conceal dangerous and underlying heating conditions on the patient's skin, and skin contact points can sometimes be shielded from thermal imaging yet still result in burns between those skin contact points (for example, thumbs on thighs, in some cases). The processor 20 can differentiate these conditions and determine underlying body temperatures. The processor 20 can additionally determine the angle of incidence in the air pockets adjacent to the patient's body and the angle of incidence in the creases and folds in the fabric. Patient movement is also tracked by the processor 20 to account for changes in attenuation for various materials that might constitute the privacy gown 24. The attenuation can be profiled, with reference to a lookup table for each of a plurality of materials that constitute each of a plurality of available privacy gowns 24. The attenuation may additionally change over the course of multiple washes, which can also be accounted for by the processor 20 when monitoring the skin surface temperature and/or the subdermal temperature.

Figure 5:
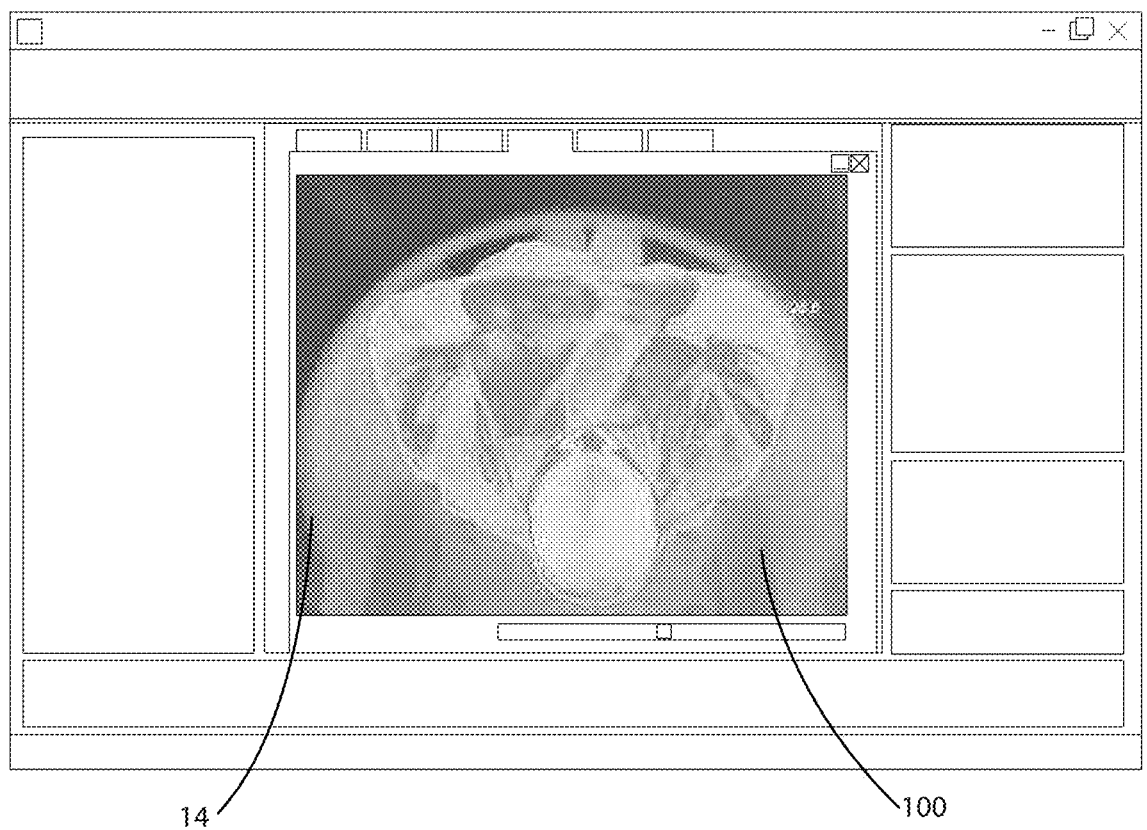
FIG. 5 is a thermographic image of a patient captured by an infrared camera while the patient undergoes an MRI.

The thermographic image optionally is presented to the operator of the MRI machine. As shown in FIG. 5, for example, the thermographic image depicts the relative temperatures of the patient according to a violet-to-white color scale. Simultaneously with the display of the thermographic image, the processor 20 can alter one or more camera operating parameters for improved detection of potential unsafe skin conditions. The camera operating parameters optionally can include the camera viewing angle, the camera lens tilt angle, the scanning frequency and/or the camera field of view. Changes in the operating parameters can be prompted by a potentially unsafe condition, for example a localized hot spot on the patient. Changes in the operating parameters optionally are pre-programmed to improve detection of a potential unsafe condition. For example, the camera lens tilt angle can vary to improve spectral acquisition of the infrared energy from the patient 100 within the barrel 14. Further by example, the camera viewing angle can increase and decrease in a vertical sweep within the plane defined by the central axis 16. Even further by example, the camera operating parameters can be adjusted to address anomalies detected during scanning. Still further by example, the camera viewing angle can increase or decrease to align the camera with a localized hot spot on the patient. Alignment of the camera with the localized hot spot is optionally accompanied by a narrowing of the field of view, adjustment of the lens tilt angle, adjustment of the camera viewing angle, and/or an increase in refresh rate to provide improved resolution and detection of the hot spot. The camera operating parameters can therefore be tailored for a full body scan of each particular patient, while also being adapted for a more detailed scan of any localized hot spots or areas prone to hot spots, for example the armpits, the wrists, and the hands. The camera operating parameters also accommodate patients of varying sizes within the MRI barrel 12, including pediatric patients, adolescent patients, and adult patients.

Further by example, FIGS. 18-21 include flow charts illustrating algorithms for monitoring one or more regions of interest (ROI), the algorithms being performed by the processor 20 in digital logic. Each image frame of a thermal video stream includes one or more ROIs. The ROI can be of any shape, for example rectangular or circular, less than the entirety of the image frame. For each ROI, the processor 20 determines the mean temperature of all points within the ROI boundary at a given time in order to detect an alert condition.

Figure 18:
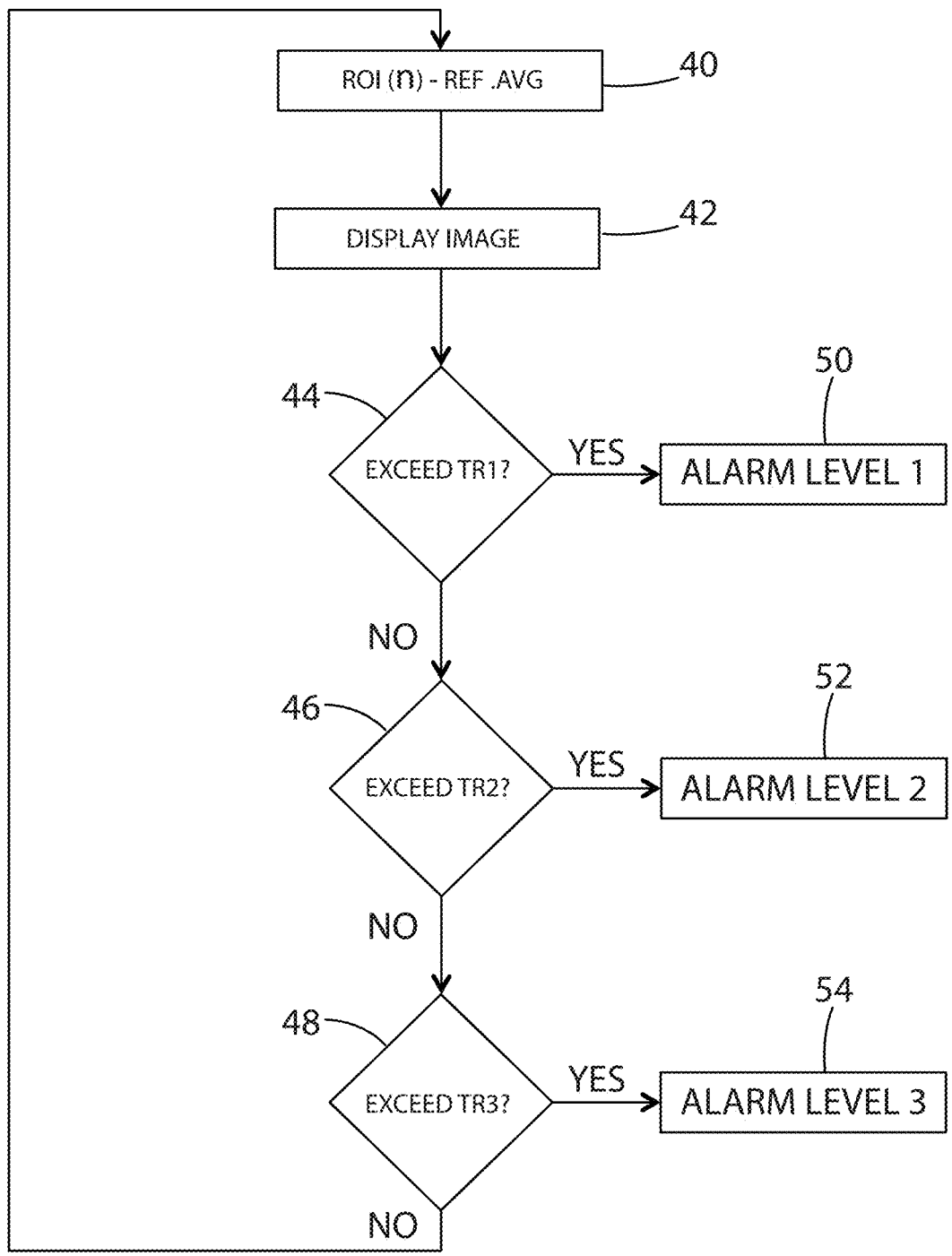
FIG. 18 is a first flow chart illustrating continuous automated monitoring of a region of interest (ROI).

Referring now to FIG. 18, a first looped algorithm is depicted, in which a reference value REF.AVG at time zero (the time at which REF.AVG was measured) is subtracted from the mean temperature within the ROI at a later time n (the current time). This operation is illustrated as step 40. At step 42, the thermal video image is displayed to the operator. The thermal video image can include an adjustable color map and adjustable threshold values. A three-tiered alarm is provided at decision steps 44, 46, and 48. At decision step 44, the output of operation step 40 is compared against TR1 (a first threshold value stored in memory, e.g., 50 degrees Celsius). If the output of decision step 44 is greater than TR1, the first alarm is output to the operator at step 50, optionally in the form of an audible alert and/or a visual alert. If the output of operation step 40 is not greater than TR1, the algorithm proceeds to decision step 46. At decision step 46, the output of operation step 40 is compared against TR2 (a second threshold value stored in memory, e.g., 40 degrees Celsius). If the output of decision step 46 is greater than TR2, the second alarm is output to the operator at step 52. If the output of decision step 46 is not greater than TR2, the algorithm proceeds to decision step 48. At decision step 48, the output of operation step 40 is compared against TR3 (a third threshold value stored in memory, e.g., 30 degrees Celsius). If the output of operation step 40 is greater than TR3, the third alarm is output to the operator at step 54. The looped algorithm then resumes at operation step 40, with REF.AVG being constant throughout the execution of the algorithm.

Figure 19:
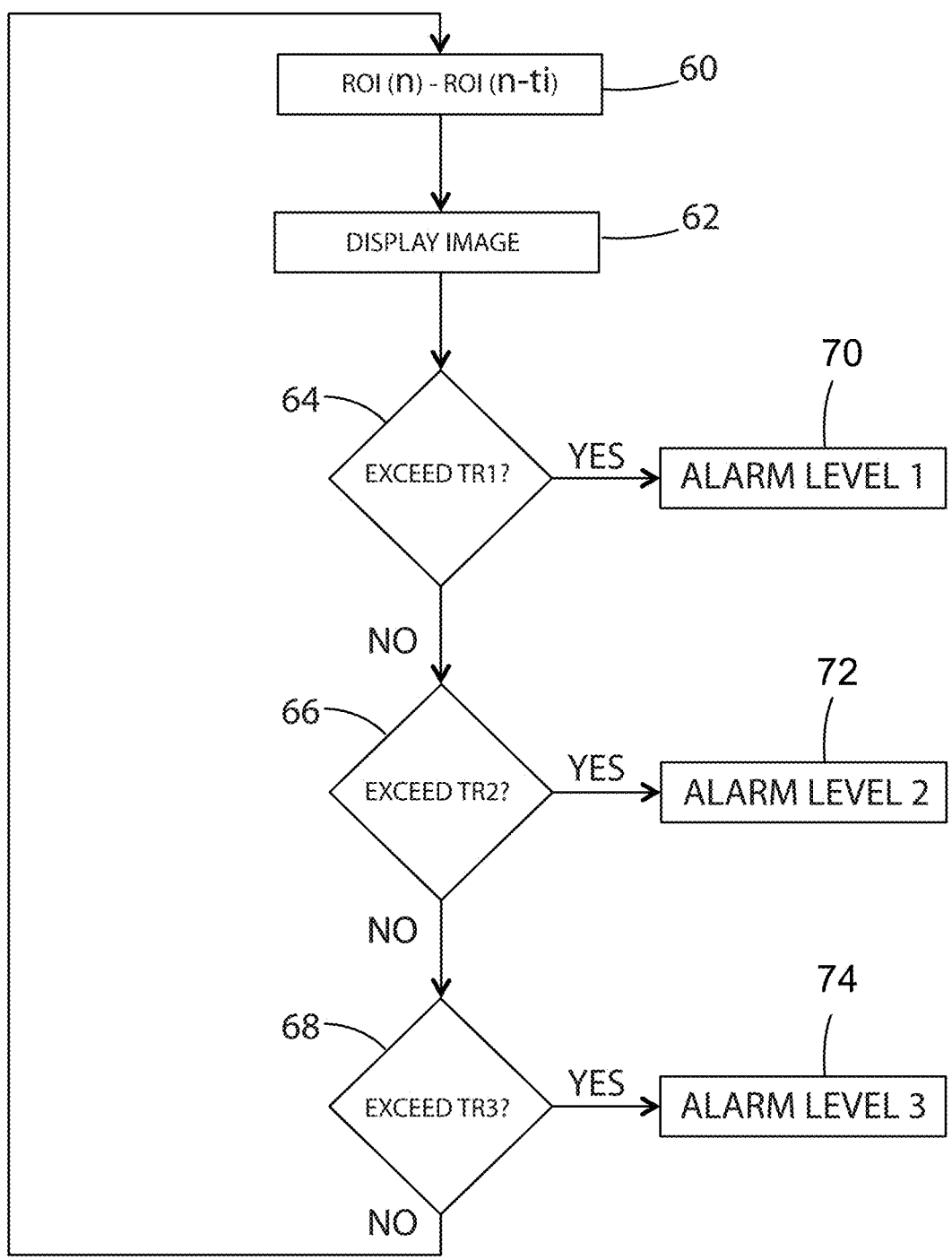
FIG. 19 is a second flow chart illustrating continuous automated monitoring of a ROI.

Referring now to FIG. 19, a second looped algorithm is depicted, in which the reference value is regularly updated. In particular, the reference value ROI(n−ti) in this second looped algorithm is the mean temperature at time n minus ti, where ti is a fixed time interval, for example 4 seconds, 40 seconds, or 4 minutes, and n is the current time. As a result, the reference value ROI(n−ti) can be said to be a sliding reference value, rather than the static reference value REF.AVG of FIG. 18. At step 60, the reference value ROI(n−ti) is subtracted from the measured value ROI(n). At step 62, the thermal video image is displayed to the operator. A three-tiered alarm is provided at decision steps 64, 66, and 68. At decision step 64, the output of operation step 60 is compared against TR1 (a first threshold value stored in memory, e.g., 50 degrees Celsius). If the output of decision step 64 is greater than TR1, the first alarm is output to the operator at step 70. If the output of operation step 60 is not greater than TR1, the algorithm proceeds to decision step 66. At decision step 66, the output of operation step 60 is compared against TR2 (a second threshold value stored in memory, e.g., 40 degrees Celsius). If the output of decision step 66 is greater than TR2, the second alarm is output to the operator at step 72. If the output of decision step 66 is not greater than TR2, the algorithm proceeds to decision step 68. At decision step 68, the output of operation step 60 is compared against TR3 (a third threshold value stored in memory, e.g., 30 degrees Celsius). If the output of operation step 60 is greater than TR3, the third alarm is output to the operator at step 74. The looped algorithm then resumes at operation step 60, with the reference value ROI(n−ti) being updated for each iteration of the algorithm.

Figure 20:
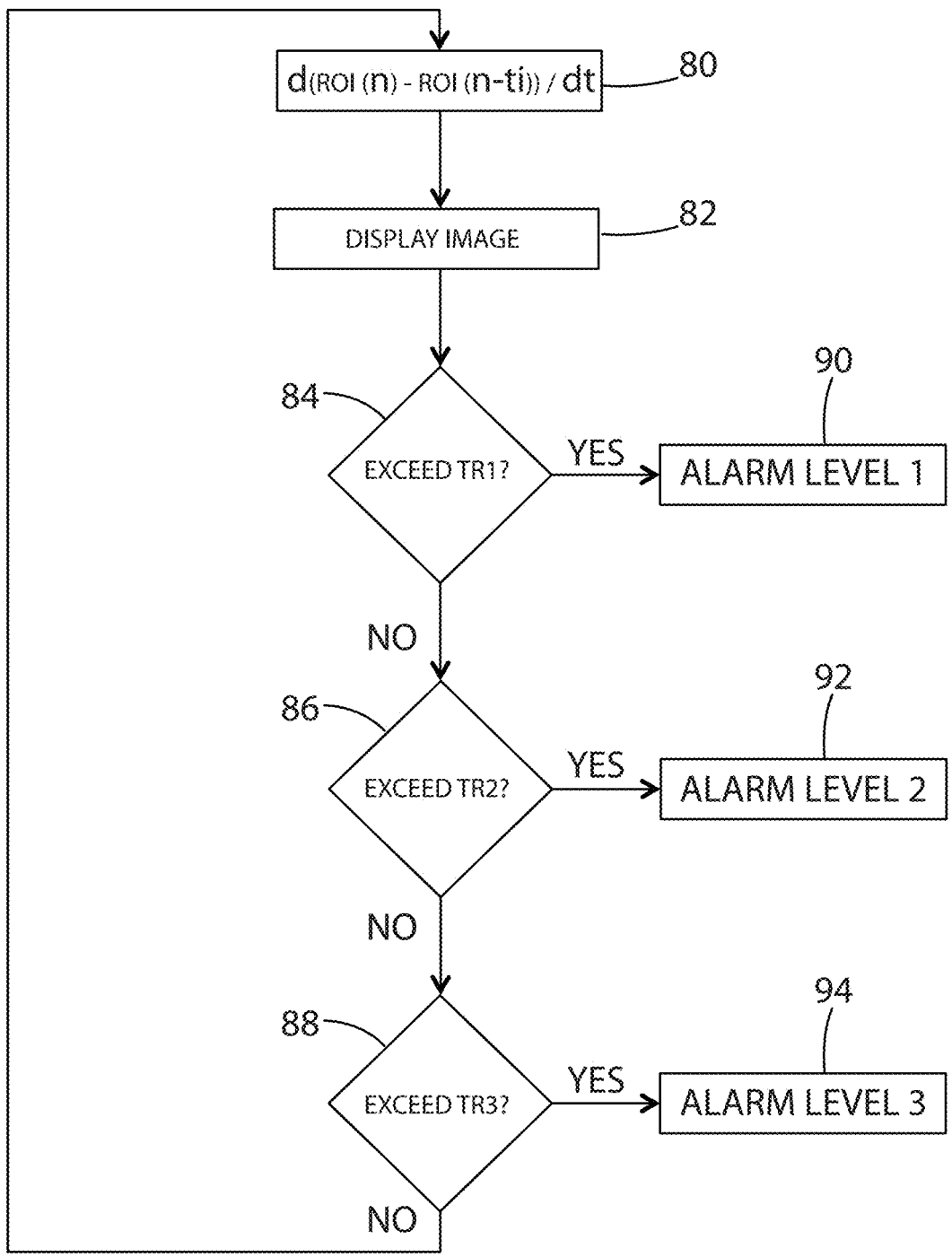
FIG. 20 is a third flow chart illustrating continuous automated monitoring of a ROI.

Referring now to FIG. 20, a third looped algorithm is depicted, in which the processor 20 determines the rate of change of the mean temperature within the ROI. At step 80, the processor 20 determines the time derivative of the temperature change, where the temperature change is measured as ROI(n)−ROI(n−ti). The time derivative is determined at time n for time interval dt. At step 82, the thermal video image is displayed to the operator. A three-tiered alarm is provided at decision steps 84, 86, and 88. At decision step 84, the output of operation step 80 (the time derivative) is compared against TR1 (a first threshold value stored in memory, in degrees Celsius per second). If the output of decision step 84 is greater than TR1, the first alarm is output to the operator at step 90. If the output of operation step 80 is not greater than TR1, the algorithm proceeds to decision step 86. At decision step 86, the output of operation step 80 is compared against TR2 (a second threshold value stored in memory, in degrees Celsius per second). If the output of decision step 86 is greater than TR2, the second alarm is output to the operator at step 92. If the output of decision step 86 is not greater than TR2, the algorithm proceeds to decision step 88. At decision step 88, the output of operation step 80 is compared against TR3 (a third threshold value stored in memory, in degrees Celsius per second). If the output of operation step 80 is greater than TR3, the third alarm is output to the operator at step 94. The looped algorithm then resumes at operation step 80 for a new value of n.

Figure 21:
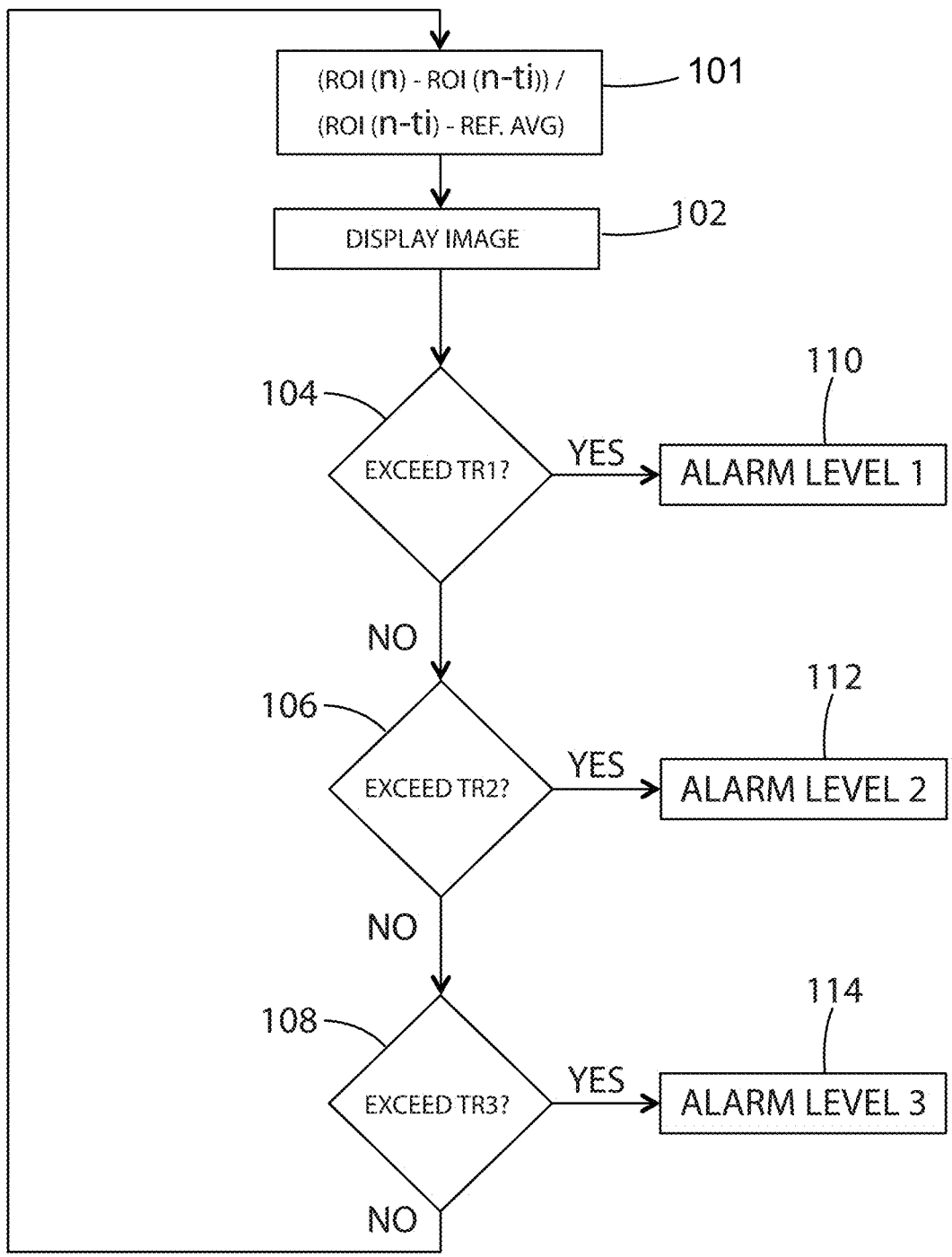
FIG. 21 is a fourth flow chart illustrating continuous automated monitoring of a ROI.
Figure 22:
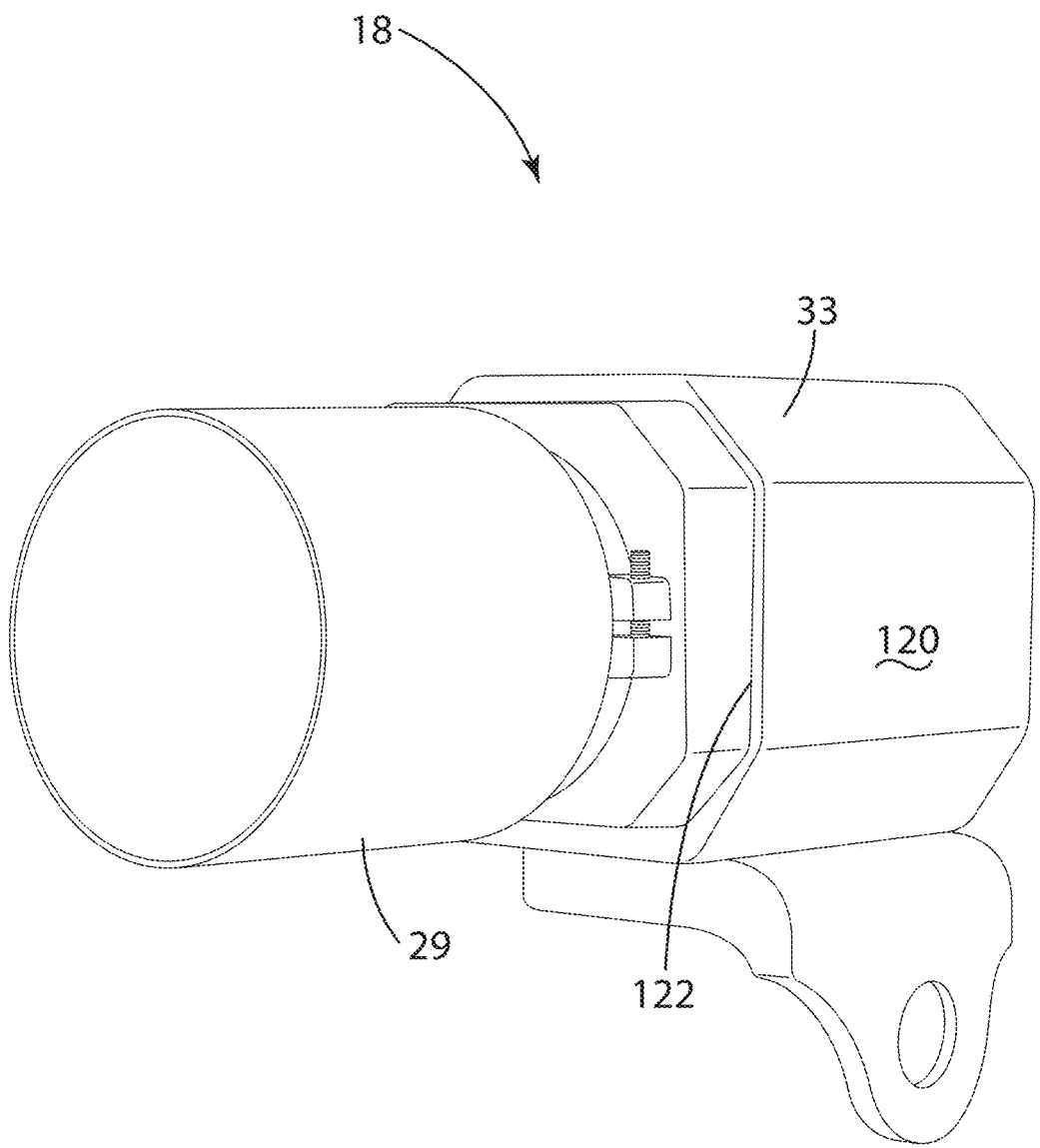
FIG. 22 is a perspective view of a thermal camera including a Faraday cage.

Referring now to FIG. 21, a fourth looped algorithm is depicted, in which the processor 20 determines at step 101 the quotient of the short term temperature change (ROI(n)−ROI(n−ti)) divided by the long term temperature change (ROI(n−ti)−REF.AVG). This operation can compensate for fabric attenuation by assuming that the body has a uniform temperature at time ti. In reality, however, the body will not have a uniform temperature within most ROIs, which can result in an overestimate of the colder areas within some ROIs. At step 102, the thermal video image is displayed to the operator. A three-tiered alarm is provided at decision steps 104, 106, and 108. At decision step 104, the output of operation step 101 is compared against TR1 (a first threshold value stored in memory, dimensionless). If the output of decision step 104 is greater than TR1, the first alarm is output to the operator at step 110. If the output of operation step 101 is not greater than TR1, the algorithm proceeds to decision step 106. At decision step 106, the output of operation step 101 is compared against TR2 (a second threshold value stored in memory, dimensionless). If the output of decision step 106 is greater than TR2, the second alarm is output to the operator at step 112. If the output of decision step 106 is not greater than TR2, the algorithm proceeds to decision step 108. At decision step 108, the output of operation step 101 is compared against TR3 (a third threshold value stored in memory, dimensionless). If the output of operation step 101 is greater than TR3, the third alarm is output to the operator at step 114. The looped algorithm then resumes at operation step 101.

The above algorithms can be performed simultaneously using logical operators to further evaluate for certain alarm conditions. For example, using the AND operator, the processor 20 can generate an alarm if decision step 68 determines that the ROI temperature has increased more than 30° C. over the last sixty seconds AND if decision step 88 determines that the ROI temperature has increased at a rate of more than 1° C. per second. Further by example, using the OR operator, the processor 20 can generate an alarm if decision step 68 determines that the ROI temperature has increased more than 30° C. over the last sixty seconds OR if decision step 86 determines that the ROI temperature has increased at a rate of more than 2° C. per second. Additionally, an alarm condition in one algorithm can prompt the processor 20 to execute one or more of the remaining algorithms. For example, if decision step 44 determines that the ROI temperature has increased more than 50° C., the processor 20 can execute the third algorithm and monitor the rate of change of ROI temperature. Further by example, if decision step 44 determines that the ROI temperature has increased more than 40° C., but less than 50° C., the processor 20 can execute the second algorithm and monitor the short term ROI temperature change (ROI(n)−ROI(n−ti)). Other combinations can be used in other embodiments as desired.

Controlling MRI imaging in response to an unsafe skin surface temperature is depicted as step 38 in FIG. 4. This step generally includes reducing the RF energy applied to the patient in response to the surface temperature exceeding a threshold temperature. This step is optionally performed automatically by the processor 20 in some embodiments. In other embodiments, the MRI operator is alerted to a potentially unsafe skin surface and/or subdermal temperature and manually reduces the RF energy applied to the patient. The alert can be in the form of a visual alert, an audible alert, a vibratory alert, or any combinations thereof.

Though described above as pertaining to an increase in temperature related to potential patient burns during MRI imaging, the current embodiments are equally well suited to monitor a drop in temperature. For example, a drop in skin surface temperature may indicate a drop in overall body temperature, which may negatively impact the efficacy of one or more drugs. For example, the effectiveness of anesthesia in pediatric patients can suffer in response to a decline in body temperature. To guard against a drop in body temperature to unacceptable or unsafe levels, the system and method of the current embodiments can remotely monitor the patient for a drop in temperature using the infrared cameras 18, 19 and processor 20 described above. Monitoring the patient for a drop in temperature is in conjunction with an MRI in some embodiments, while being separate from an MRI in other embodiments.

EXAMPLE

The current embodiments are further illustrated by the following example, which is intended to be non-limiting.

Figure 13:
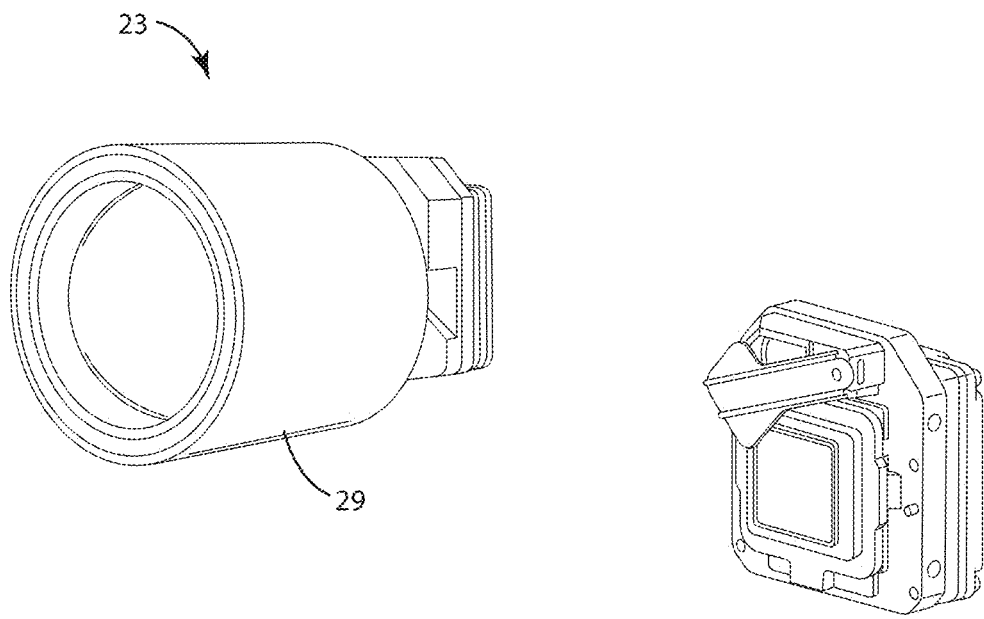
FIG. 13 is an illustration of an infrared camera in accordance with an example of the present invention.

An infrared camera including a tilt lens was selected for thermal imaging of an MRI barrel. The infrared camera included the Tau 640 thermal imaging camera (from FLIR Systems, Inc.). The Tau 640 included a two-dimensional array 31 with 640×512 elements. Additional camera parameters are illustrated in FIG. 13, including a field of view of 12.4°×9.9° with a 50 mm equivalent focal length. The camera was provided with a 60 mm LWIR tilt lens 23, which is illustrated in FIG. 14, having a focal ratio of 1.2 and a focal length of 50 mm.

Figure 15:
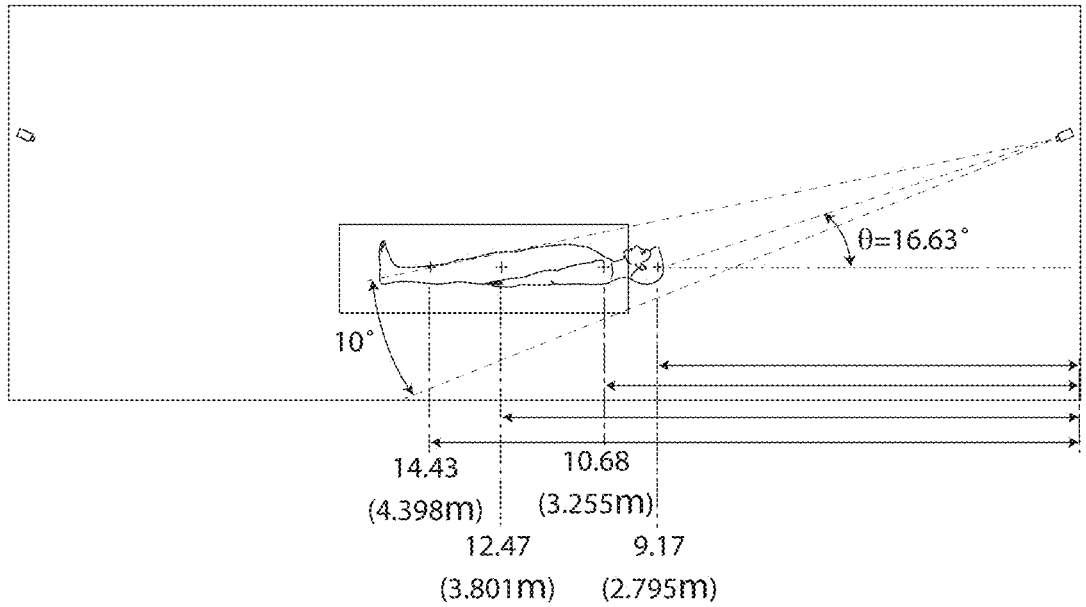
FIG. 15 is a side view of an MRI procedure room layout illustrating the infrared camera of FIG. 13 oriented toward an MRI Barrel.
Figure 16:
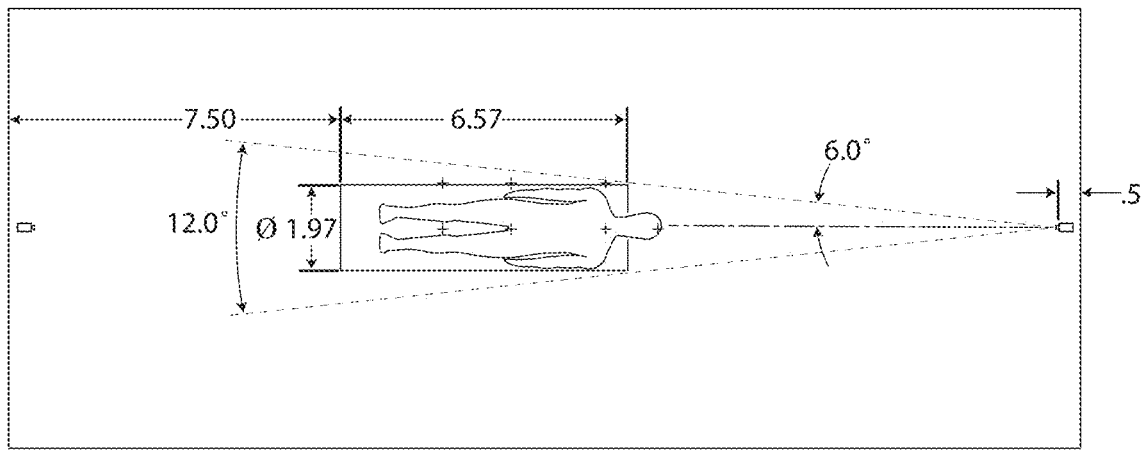
FIG. 16 is a top view of an MRI procedure room layout illustrating the infrared camera of FIG. 13 oriented toward an MRI Barrel.
Figure 17:
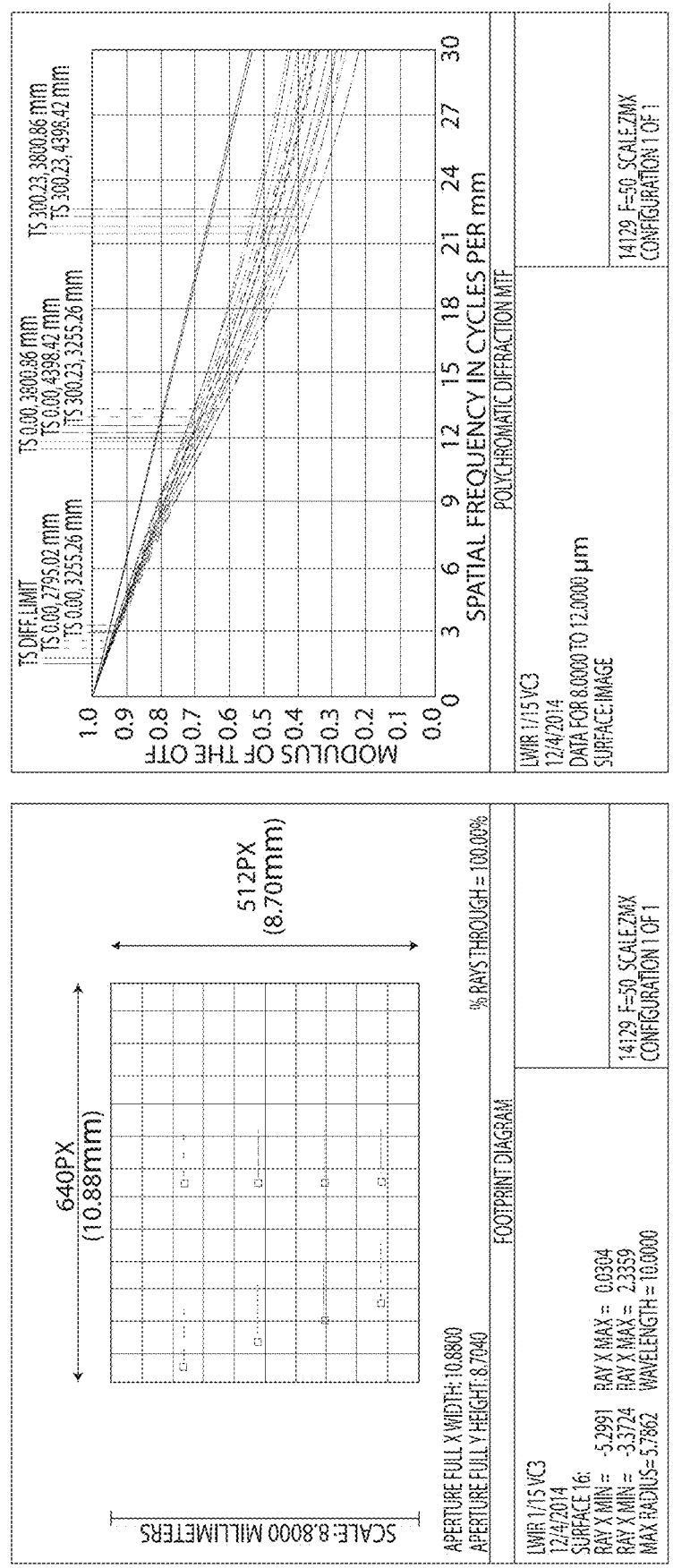
FIG. 17 is a graph illustrating the modulation transfer function for the infrared camera of FIG. 13 in the MRI procedure room of FIGS. 15-16.

The infrared camera was vertically offset from the central axis of the barrel by a distance of 2.97 feet, horizontally from the head by a distance of 9.17 feet, horizontally offset from the shoulders by a distance of 10.68 feet, horizontally offset from the groin by a distance of 12.47 feet, and horizontally offset from the head by a distance of 14.43 feet. These field points are illustrated in FIGS. 15-16. A further set of three field points were laterally offset from the central axis of the barrel, simulating the location of the patient's upper extremities. The infrared camera provided the best focus with a 3° (clockwise) tilt of the backend, from the aperture stop to the detector plane. Results are indicated in FIG. 17. The infrared camera demonstrated excellent performance (contrast) on the MTF graph of FIG. 17, corresponding to excellent focus at each of the seven field points of FIGS. 15-16.

The system and method of the current embodiments therefore provide improved detection of RF burns during MRI imaging, including preventative wide-area scans and reactive small-area scans of localized hot spots. The system and method of the current embodiments are well suited for adult patients, adolescent patients and pediatric patients. With improved detection of skin surface and/or subdermal temperatures during MRI imaging, the current embodiments can reduce the incidence of RF burns while not otherwise interfering with MRI procedures.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A method of performing magnetic resonance imaging (MRI) without burning a patient with associated radio-frequency (RF) energy comprising:
   providing an MRI device having a patient barrel, the patient barrel defining a central longitudinal axis;
   positioning an infrared camera outside of the patient barrel and above the central longitudinal axis of the patient barrel, the infrared camera comprising a thermal video camera and is vertically offset from the central longitudinal axis of the patient barrel and has a line of sight oriented downward at an angle relative to the central longitudinal axis of the patient barrel, the infrared camera having a field of view, the infrared camera providing an output to a processor, wherein the output includes at least a plurality of image frames from a thermal video stream of the patient barrel, wherein each of the plurality of image frames includes a first region of interest and a second region of interest, wherein the first region of interest and the second region of interest each include a plurality of points within a boundary, such that the first region of interest includes a first plurality of points within a first boundary and the second region of interest includes a second plurality of points within a second boundary;
   performing an MRI scan of a patient in the patient barrel to obtain an MRI image of at least a portion of the patient;
   monitoring, with the processor, based on the output of the infrared camera during the MRI scan, a first mean surface temperature of the first plurality of points within the first region of interest in an image frame and a second mean surface temperature of the second plurality of points within the second region of interest in the image frame;
   determining a rate of change in the first mean surface temperature relative to a prior mean temperature within the first region of interest and determining a rate of change in the second mean surface temperature relative to a prior mean temperature within the second region of interest;
   comparing the rate of change in the mean surface temperature for each of the first and second regions of interest with a plurality of tiered threshold values for the respective region of interest, wherein the processor performs a modulation transfer function to perform the comparison of the rate of change in the mean surface temperature for each of the first and second regions of interest with the plurality of tiered threshold values for the respective region of interest;
   causing an alert if the rate of change in the mean surface temperature exceeds any one of the plurality of tiered threshold values for any one of the first or second regions of interest; and
   altering the field of view of the infrared camera during the MRI scan to provide observation at multiple locations of the patient within the patient barrel of the MRI device.

2. The method of claim 1, further comprising donning the patient with an infrared transmissive gown that allows infrared wavelengths to pass through it, but provides visual concealment of the patient.

3. The method of claim 1, wherein the angle is defined between the line of sight of the infrared camera and the central longitudinal axis of the patient barrel is a viewing angle, the method further comprising adjusting the viewing angle to image the patient within the patient barrel.

4. The method of claim 1, further comprising:
   defining a lens tilt angle of the infrared camera; and
   adjusting the lens tilt angle to image the patient within the patient barrel.

5. The method of claim 1, further including terminating the MRI scan in response to the rate of change in the first or second mean surface temperature exceeding any one of the plurality of tiered threshold values for the respective region of interest.

6. A system for monitoring a patient undergoing magnetic resonance imaging (MRI), the system comprising:
   a patient barrel arranged to surround a patient, the patient barrel defining a central longitudinal axis;
   an infrared camera configured to image the patient and having a field of view, the infrared camera comprising a thermal video camera being positioned outside of the patient barrel and above the central longitudinal axis of the patient barrel and including an output, such that the infrared camera is vertically offset from the central longitudinal axis of the patient barrel and has a line of sight oriented downward at an angle relative to the central longitudinal axis of the patient barrel, the output including at least a plurality of image frames from a thermal video stream of the patient barrel, wherein each of the plurality of image frames includes a first region of interest and a second region of interest, wherein the first region of interest and the second region of interest each include a plurality of points within a boundary, such that the first region of interest includes a first plurality of points within a first boundary and the second region of interest includes a second plurality of points within a second boundary; and
   a processor adapted to:
      monitor a first mean surface temperature of the first plurality of points within the first region of interest and a second mean surface temperature of the second plurality of points within the second region of interest based on the output of the infrared camera during magnetic resonance imaging of the patient;
      determine a rate of change of the first mean surface temperature relative to a prior mean surface temperature within the first region of interest and determine a rate of change of the second mean surface temperature relative to a prior mean surface temperature within the second region of interest;
      compare the rate of change in the mean surface temperature for each of the first and second regions of interest with a plurality of tiered threshold values for the respective region of interest, wherein the processor performs a modulation transfer function to compare the rate of change in the mean surface temperature for each of the first and second regions of interest with the plurality of tiered threshold values for the respective region of interest;
      cause an alert if the rate of change in the mean surface temperature exceeds any one of the plurality of tiered threshold values for any one of the first or second regions of interest; and alter the field of view of the infrared camera during magnetic resonance imaging of the patient to provide observation at multiple locations of the patient within the patient barrel.

7. The system of claim 6, wherein the processor is further adapted to terminate magnetic resonance imaging of the patient in response to the rate of change in the mean surface temperature exceeding any one of the plurality of tiered threshold values for any one of the first or second regions of interest.

8. The system of claim 6, wherein the processor is further adapted to generate a computer model of the first mean surface temperature and the second mean surface temperature.

9. The system of claim 6, further comprising a patient gown formed of an infrared transmissive material for wavelengths between 8 microns and 14 microns, inclusive.

10. The system of claim 9, wherein the patient gown is formed of at least one of polyethylene, polypropylene, and combinations thereof.

11. The system of claim 6, further including an electrically conductive enclosure at least partially housing the infrared camera therein.

12. The system of claim 6, wherein the infrared camera includes an adjustable scanning frequency.

13. The system of claim 6, wherein the infrared camera includes an adjustable lens tilt angle.

* * * * *